(12) United States Patent
Hallett et al.

(10) Patent No.: US 9,308,344 B2
(45) Date of Patent: Apr. 12, 2016

(54) RESPIRATORY VALVE APPARATUS

(75) Inventors: Michael David Hallett, Pyrmont (AU); Michael Kassipillai Gunaratnam, Marsfield (AU); Allan Nils Gregersen, Auckland (NZ)

(73) Assignee: VENTIFIC HOLDINGS PTY LTD, Pyrmont (AU)

( * ) Notice: Subject to any disclaimer, the term of this patent is extended or adjusted under 35 U.S.C. 154(b) by 298 days.

(21) Appl. No.: 13/518,553

(22) PCT Filed: Aug. 26, 2011

(86) PCT No.: PCT/AU2011/001094
§ 371 (c)(1),
(2), (4) Date: Jun. 22, 2012

(87) PCT Pub. No.: WO2012/048364
PCT Pub. Date: Apr. 19, 2012

(65) Prior Publication Data
US 2013/0186394 A1 Jul. 25, 2013
US 2014/0109901 A9 Apr. 24, 2014

Related U.S. Application Data

(60) Provisional application No. 61/392,954, filed on Oct. 14, 2010.

(51) Int. Cl.
*A62B 9/02* (2006.01)
*A61M 16/20* (2006.01)
(Continued)

(52) U.S. Cl.
CPC ........... *A61M 16/20* (2013.01); *A61M 16/0057* (2013.01); *A61M 16/06* (2013.01);
(Continued)

(58) Field of Classification Search
CPC  A61M 16/206; A61M 16/207; A61M 16/208
See application file for complete search history.

(56) References Cited

U.S. PATENT DOCUMENTS

| 4,088,131 A * | 5/1978 | Elam ................. A61M 16/0084 128/205.13 |
| 4,259,951 A | 4/1981 | Chernack et al. |

(Continued)

FOREIGN PATENT DOCUMENTS

| GB | 748363 A | 5/1956 |
| GB | 799225 A | 8/1958 |

(Continued)

OTHER PUBLICATIONS

International Search Report (ISR) of Sep. 26, 2011 in PCT/AU2011/001094.

(Continued)

*Primary Examiner* — Tan-Uyen (Jackie) T Ho
*Assistant Examiner* — Aundria Hairell
(74) *Attorney, Agent, or Firm* — Young Law Firm, P.C.

(57) ABSTRACT

The invention relates to a pressure responsive respiratory valve apparatus for enabling positive pressure from a source of pressure to be applied to a user's airway, and allowing ingress of a breathable gas from an inlet port into a user's airway during inhalation and egress of expired tidal volume of air from the user's respiratory system to an exhalation port during exhalation. The invention minimises rebreathing of expired gas and optimizes delivery of pressurised breathable gas by venting gas only during exhalation, as well as addressing important user considerations including minimizing noise, pressure swing, and size.

21 Claims, 19 Drawing Sheets

(51) Int. Cl.
  *A61M 16/06* (2006.01)
  *A61M 16/00* (2006.01)
  *A61M 16/10* (2006.01)
  *A61M 16/08* (2006.01)

(52) U.S. Cl.
  CPC ......... *A61M16/0666* (2013.01); *A61M 16/201* (2014.02); *A61M 16/206* (2014.02); *A61M 16/0816* (2013.01); *A61M 16/1045* (2013.01); *A61M 16/208* (2013.01); *A61M 2202/0225* (2013.01)

(56) References Cited

U.S. PATENT DOCUMENTS

| | | | |
|---|---|---|---|
| 5,398,673 A | 3/1995 | Lambert | |
| 5,603,314 A | 2/1997 | Bono | |
| 5,906,203 A * | 5/1999 | Klockseth et al. | 128/205.24 |
| 2003/0221691 A1 * | 12/2003 | Biener et al. | 128/206.24 |
| 2005/0172969 A1 * | 8/2005 | Ging et al. | 128/206.24 |
| 2008/0142013 A1 | 6/2008 | Hallett et al. | |
| 2008/0190429 A1 * | 8/2008 | Tatarek | 128/204.23 |
| 2009/0133700 A1 * | 5/2009 | Martin et al. | 128/207.12 |
| 2009/0260628 A1 * | 10/2009 | Flynn, Sr. | A61M 16/0078 128/203.28 |
| 2010/0199985 A1 | 8/2010 | Hamilton et al. | |

FOREIGN PATENT DOCUMENTS

| | | | |
|---|---|---|---|
| GB | 2416701 A | 2/2006 | |
| WO | WO 2008114079 A1 * | 9/2008 | A61M 16/00 |
| WO | 2009/017952 A2 | 2/2009 | |
| WO | 2010/061173 A1 | 6/2010 | |

OTHER PUBLICATIONS

International Preliminary Report on Patentability of Jan. 16, 2012 in PCT/AU2011/001094.

* cited by examiner

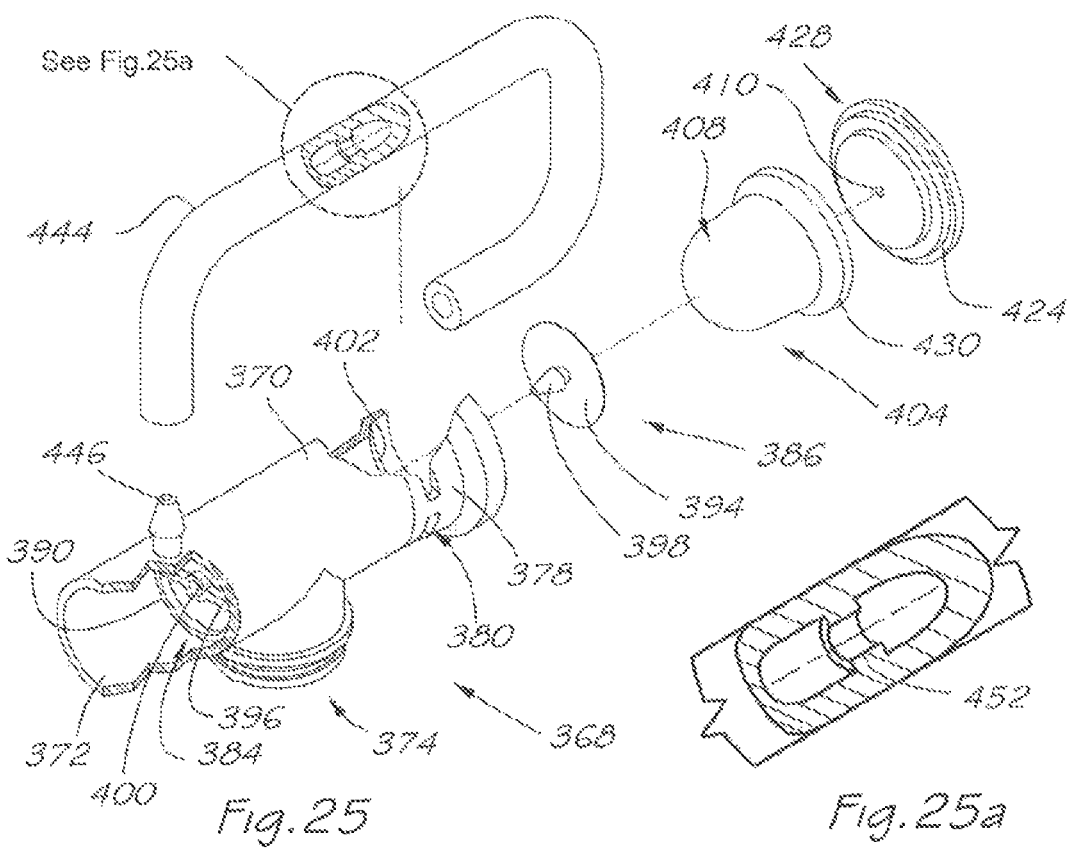
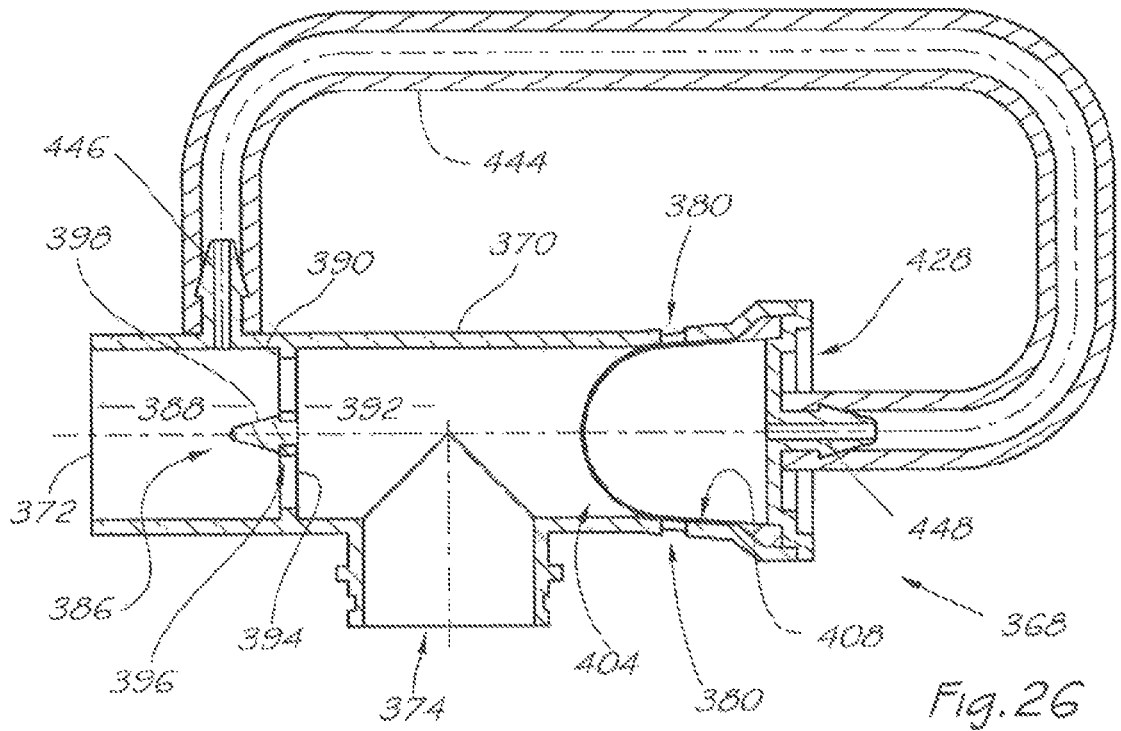

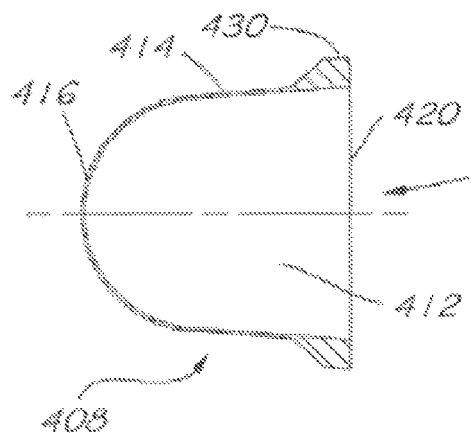
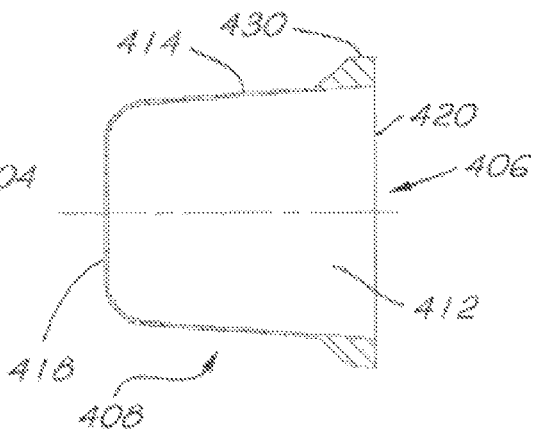
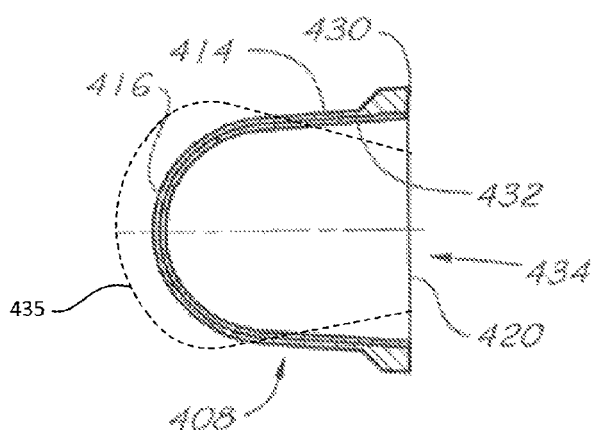
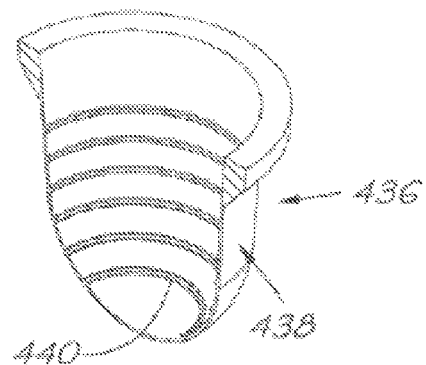
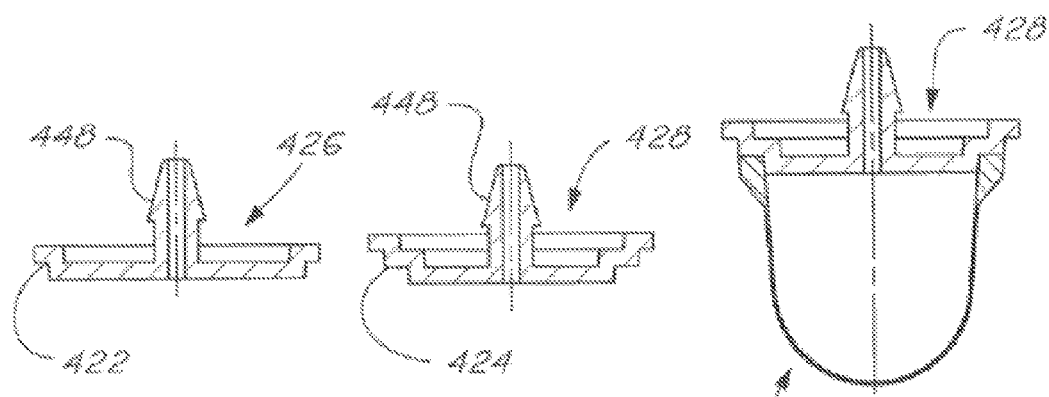
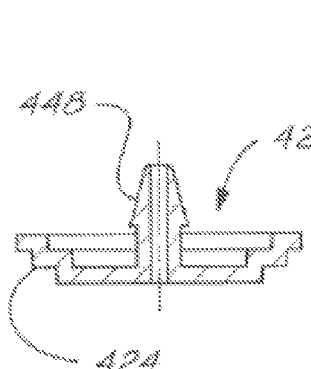
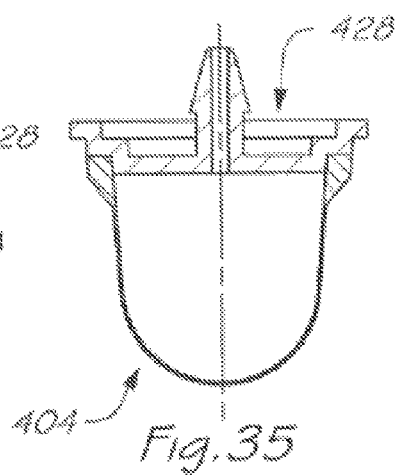

RESPIRATORY VALVE APPARATUS

CROSS REFERENCE TO RELATED APPLICATIONS

This application is a 35 USC §371 US National Phase application of serial number PCT/AU2011/001094 having an International Filing Date of 26 Aug. 2011 and claims priority under 35 USC §119(e) to U.S. Provisional Patent Application No. 61/392,954 filed 14 Oct. 2010.

FIELD OF THE INVENTION

The present invention relates broadly to a respiratory valve apparatus. The present invention is in the field of positive pressure respiratory therapy such as nasal CPAP or positive pressure ventilation, as may be applied to a user through a user interface, such as a nasal mask, oronasal mask, nasal prongs or suitable invasive means, such as tracheostomy or endotracheal tube.

TECHNICAL BACKGROUND

Positive pressure respiratory therapies, such as continuous positive airway pressure (CPAP) therapy, and intermittent positive pressure ventilation therapy (IPPV), are commonly administered for the treatment of a wide range of respiratory conditions, including central and obstructive sleep apnea. (OSA), chronic obstructive pulmonary disease (COPD), restrictive respiratory insufficiency and acute respiratory failure (ARF). Acute and chronic life support systems also make use of positive 15 pressure respiratory therapies using volume or pressure controlled cycles. Typically, positive pressure delivered via an externally fitted interface such as a removable face mask, for example, would be used to provide intermittent positive pressure treatment of responsive conditions in a conscious user, that is, when the user is either awake or asleep, but otherwise fully arousable and able to sustain at least partial respiratory effort. Tracheostomy may be required for chronic life support involving, for example, total loss of respiratory muscle innervation. In temporarily anesthetised or otherwise unconscious users without sufficient self-supporting respiratory drive or those with unstable airways, ventilation would normally be accomplished with an invasive interface means, such as an endotracheal tube or pharyngeal mask, to ensure reliable connection of the pressure source and hence predictable ventilation. In general it is preferable to adopt the least invasive means to treat a specific condition in order to mitigate complications, complexity and cost of care. For this reason, the application of externally sealing face masks has become increasing popular in hospital settings where feasible. Examples include ventilation with full face or nasal masks for management of acute respiratory failure. Additional benefits of non-invasive positive pressure treatment methods include their improved applicability to use in a home setting where ease of use, comfort and efficacy are key factors in determining patient compliance with therapy. The ability to treat chronic disorders in the convenience of the home setting improves long-term health outcomes for users and relieves the burden on hospital resources.

Any gas pressure delivering means can be used as the source of positive pressure. In the prior art, a pressure source would typically comprise a gas flow generator and a gas flow circuit in the form of a flexible air delivery hose which connects the gas flow generator to a user interface. If a gas flow generator is made small enough it could be attached directly to, or integrated with, the user interface, and then it alone would comprise the positive pressure source. Where a. primary gas flow delivery tube is used it may include a. secondary tube or limb to recover or direct expired gas as may be used with anesthesia or ventilation. In the case of nasal CPAP therapy, a source of breathable gas maintained at a substantially constant treatment pressure above atmospheric pressure over a breathing cycle, is applied to a user's airway via a user interface, such as a nasal mask, mouth mask, oronasal mask, nasal prongs or other externally fitted device. CPAP therapy is most commonly used to treat OSA in a home-care s setting, although it is also applicable to a variety of other respiratory conditions. CPAP therapy, particularly for home use, may also include limited pressure release modes, whereby treatment pressure is reduced during exhalation and restored to its previous preexhalation level at the end of expiration. This approach offers less resistance to expiratory effort and is intended to either enhance breathing comfort in the case of sleep apnea, or, to assist or support a user's own respiratory effort in the case of respiratory insufficiency. The latter case is often termed bi-level treatment to reflect the fact that distinct pressures are applied to a user's airway during a single breathing cycle. Pressures may also be varied as a function of time and flow, in which cases there may be a range of pressure applied during a single breathing cycle. To facilitate venting of expired tidal volume from a user's airway when using an externally fitted user interface, it typically will have incorporated into its structure a vent or vents of fixed dimension which are open to atmosphere. In this way, a breathable gas is able to leak from the vents continuously under the effect of the positive pressure applied to the user interface from the pressure source. The magnitude of this vented flow of breathable gas to atmosphere will be a function of the pressure within the user interface and vent configuration. Typically, designers will attempt to find a suitable compromise between vent size and number, such that sufficient gas is vented in order to limit the amount of exhaled carbon dioxide ($CO_2$) which is rebreathed by the user, whilst keeping the magnitude of vented gas low enough not to require a significant increase in pressure source capacity to compensate for this operational leak. For example, at a user interface pressure of 10 cm of water, the vent flow rate may be in the order of 20 liters/min whereas at 20 cm of water it may be in the order 60 liters/min. These figures assume that there is no additional unintended leak, as may be attributable to a poorly fitting user interface. An absence of means to physically prevent reverse flow of expired gas back towards the pressure source means that some fraction of a user's exhaled air may accumulate within the pressure source and thereby be re-inhaled during subsequent inhalation or lung reinflation. Additionally, some fraction of the air provided by the pressure source is directed straight to atmosphere via the vents without entering to the user's airway since it must be applied to reducing the effective total dead space of the user including the interface and pressure source. It is apparent therefore that the lower the therapeutic pressure. the less effective is the venting of stale expired gas from a user's respiratory system. This last limitation in the current state of the art requires devices to specify a minimum operating pressure in order to provide a safe level of elimination of expired tidal volume and hence prevent rebreathing of $CO_2$. Typically, this minimum pressure required from the pressure source is in the order of 4 cm of water. Prolonged use below this minimum pressure puts the user at risk of rebreathing a substantial proportion of their expired air and asphyxiation if both nose and mouth breathing routes are covered by a. well-fitting oronasal mask, for example. It is evident that the prior art exhibits further inherent limitations depending on operating circumstances.

At high rates of breathing cycles, deep breathing, or a combination of both over a prolonged period, there will be increased levels of rebreathing of expired air and CO2, thereby increasing the user's effective airway dead space, which includes the interface and pressure source. Furthermore, the capacity of the pressure source must be increased to compensate for continuously vented flow which necessarily increases with pressure as described. Additionally, when humidification is required by the user, further capability must be factored into the design of the pressure source because some varying fraction of the humidified air is vented to atmosphere through the vents without entering the user's airway, thereby requiring both heating and storage of an additional volume of water that is not used to humidify a user's airway. Similarly, if required, flow of instilled supplementary therapeutic gases, for example oxygen, or other therapeutic substances must also be correspondingly increased to compensate for loss due to continuous venting of the breathable gas.

When breathable gas exits the vents of the user interface, it typically creates noise which may irritate the user or their bed partner. The acoustic magnitude of this vent noise is proportional to the rate of vent flow. It can be further appreciated that exhaled gas combined with flow from the pressure source will exit the user interface with sufficient velocity and volume to increase the risk of spreading infectious particles if present in exhaled gas to the surrounding environment. This may pose a significant infection risk to health workers in a hospital setting and others in the vicinity. If the source of breathable gas fails to generate the prescribed minimum pressure, such as during a power failure, users fitted with a full face mask, such as one which covers both the nose and mouth, must also be fitted with an anti-asphyxia valve to ensure the user does not rebreathe a substantial part of their expired tidal volume which, in the absence of sufficient background pressure and corresponding flushing flow, will accumulate in the pressure source. A further application of the invention is bi-level therapy wherein, rather than administering a substantially constant positive pressure over a breathing cycle, pressure will be varied within a breathing cycle to assist natural breathing. As a general principle, pressure applied during lung filling or inspiration will be greater than that applied during lung emptying or expiration to facilitate gas movement into and out of a user's respiratory system. Transition from a higher to lower pressure is most often triggered by machine sensing of the user's breathing, or follows pre-set machine controlled breathing rates, pressures or volumes. Means of connecting a source of pressurised breathable gas to a user's facially accessible airway will involve a range of user interface devices similar to those described for CPAP therapy and corresponding methods of venting expired air from a user's respiratory system, that is, through a series of small vents often positioned in the interface itself. Such arrangements will suffer similar limitations to those described previously. Additionally, it can be appreciated that CO2 rebreathing may produce a more detrimental impact in bi-level therapy users due to the fact that these individuals typically exhibit a greater degree of respiratory impairment by virtue of background hypoxia, hypercapnia; more rapid breathing and perhaps exaggerated tidal volume, particularly during acute exacerbations and their prodrome. Since the pressure applied during exhalation is lower than that applied during inhalation, the ability to clear residual expired air from the system may be further compromised. A clinical compromise involves finding a suitable range of pressures to facilitate user comfort, adequate ventilation and adequate flushing of exhaled gas accumulated within the pressure source to minimize negative impacts related to CO2 rebreathing. In yet a further application, positive pressure therapies, particularly those involving ventilation, may also be administered via endotracheal tubes, laryngeal masks, tracheotomies or similar invasive means. In these circumstances, it is common to provide active venting wherein the venting of exhaled tidal volume from a user's airway is provided through an arrangement of inspiratory and/or expiratory valves placed in the breathing circuit and often under automated synchronised control from the pressure source. The prior art describes many circuit arrangements depending on the clinical requirements, including open and fully closed recirculating systems. In its simplest form an active exhalation valve will be present to direct exhaled gas to atmosphere while allowing fresh breathable gas to be supplied to the user's airway on cycling to an upper pressure. Such control means add mechanical and electrical complexity and increased risk of asphyxiation by rebreathing in the event of failure of valve actuation systems and components.

SUMMARY OF THE INVENTION

According to the present invention there is provided a respiratory valve apparatus for delivering a pressurised flow of breathable gas to the airway of a user, the respiratory valve apparatus comprising: a valve body including an inlet port for receiving the breathable gas, an outlet port for releasing the breathable gas to the user's airway during an inhalation phase and for receiving exhaled gas during an exhalation phase of the user's respiratory cycle, a breathable gas flow passage communicating between the inlet and outlet ports, an exhaust port for releasing the exhaled gas, and an exhaled gas flow passage communicating between the outlet and exhaust ports; a first valve means located in the breathable gas flow passage and being operable under the pressurised flow of breathable gas from the inlet port to open the breathable gas flow passage during the inhalation phase so as to permit flow of the breathable gas to the user, and to close the breathable gas flow passage during the exhalation phase; a second valve means located in the exhaled gas flow passage and including a flexible membrane which defines an internal cavity, the flexible membrane being operable under ambient pressure and during the inhalation phase to seal the exhaust port for its closure and during the exhalation phase to deflect to at least partly expose and open the exhaust port; an equilibrium passage disposed between an upstream side of the first valve means and the internal cavity of the second valve means and being operable under the pressurised flow of breathable gas from the inlet port to divert part of the breathable gas to the internal cavity of the flexible membrane via the equilibrium passage to at ambient pressure and during the inhalation phase maintain closure of the exhaust port.

Preferably the exhaust poll includes a plurality of substantially parallel slots spaced circumferentially around the valve body at the exhaled gas flow passage. More preferably the plurality of slots are staggered in length. Even more preferably the plurality of slots are each longitudinally tapered in thickness being progressively narrower in an upstream direction.

Preferably the flexible membrane is a flexible synthetic polymeric film of a thickness less than 0.1 mm. More preferably the synthetic polymeric film is polyethylene of a thickness less than 50 μm. Preferably the flexible membrane is a sock-like structure having an outer surface shaped substantially complementary to an inner cylindrical wall of the valve body against which it seals. More preferably the sock-like structure is tapered in shape with the flexible membrane becoming progressively smaller in circumference from its open end to its closed end. Alternatively the sock-like structure is tapered in shape with the flexible membrane becoming progressively larger in circumference from its open end to its closed end. Even more preferably the sock-like structure at or adjacent to its closed end includes an expanded annular sealing portion.

Preferably the valve body includes a humidification element coupled to the outlet port to capture moisture from the exhaled gas and transfer said moisture at least in part to inhaled Ras from the pressurized flow of breathable gas. Preferably the equilibrium passage is defined by a bias pressure passage restricted to dampen operation of the second valve means. More preferably the bias pressure passage includes a bias pressure tube. Preferably the valve body includes a swivel connector at the inlet port, the first valve means connected to the swivel connector. More preferably the first valve means is a non-return valve including a flexible flap connected to the swivel connector. Even more preferably the swivel connector includes a central post to which the flexible flap is mounted. Preferably the respiratory valve apparatus also comprises a user interface connected to the valve body. More preferably the user interface is integral with the valve body.

BRIEF DESCRIPTION OF THE DRAWINGS

Operation and design of the various aspects and embodiments of the invention are described in the following description and drawings.

FIG. 5a is an enlarged view of the detail highlighted in FIG. 5;

FIG. 16b is a detail view showing a deformation applied to the swivel connector of FIG. 15 in order to fasten the components shown in FIG. 16a;

FIG. 25 is a pictorial exploded and partly cut-away view of the respiratory valve apparatus according to a third embodiment of the present invention and showing a zone of detail is for subsequent views;

FIG. 25a is an enlarged view of a detail highlighted in FIG. 25;

FIG. 26 is a sectional side view of the respiratory valve apparatus shown in FIG. 25;

FIG. 29 is an isolated sectional side view of the flexible membrane and flange of the balanced pressure valve used in the respiratory valve apparatus of FIG. 25;

FIG. 30 is a sectional side view of another embodiment of the flexible membrane and flange of the balanced pressure valve used in the respiratory valve apparatus of FIG. 25;

FIG. 31 is a sectional side view of another embodiment of the flexible membrane and flange of the balanced pressure valve used in the respiratory valve apparatus of FIG. 25;

FIG. 32 is a pictorial and partly cut-away view of yet another embodiment of the flexible membrane used in the respiratory valve apparatus of FIG. 25;

FIG. 33 is a sectional side view of one form of barbed end cap used in the respiratory valve apparatus of FIG. 25;

FIG. 34 is a sectional side view of another form of barbed end cap used in the respiratory valve apparatus of FIG. 25;

FIG. 35 is a sectional side view of the barbed end cap shown in FIG. 34 fitted to a flexible membrane of balanced pressure valve used in the respiratory valve apparatus of FIG. 25;

DETAILED DESCRIPTION

Figure 1:
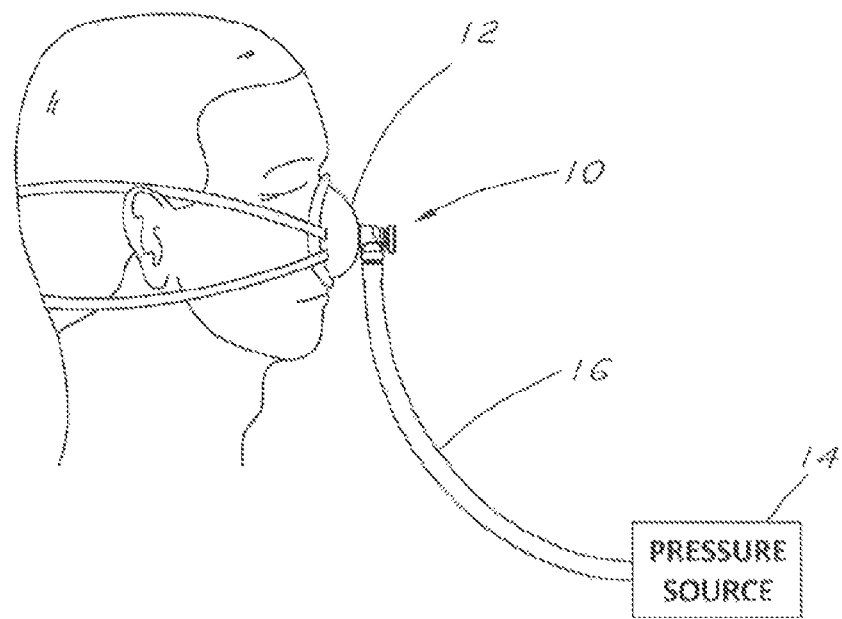
FIG. 1 is a side view of a system for providing respiratory therapy to a user that uses a respiratory valve apparatus according to a first aspect of the present invention.

A first embodiment of a respiratory valve apparatus according to a first aspect of the present invention is shown in FIGS. 1 to 7. FIG. 1 shows the apparatus 10 in use in a system for providing respiratory therapy. Apparatus 10 is coupled or sealably secured to a mask or user interface 12 covering the nose of a user, and is fed with a pressurised flow of breathable gas from a pressure source comprising gas flow generator 14 and delivery tube 16, whereby breathable gas is delivered to the airway of the user.

It will be appreciated by those skilled in the art that although a nasal user interface is depicted here, alternatives such as an oronasal, oral appliance tracheostomy or endotracheal tube may also be applicable.

The user may be an individual undergoing respiratory therapy, and the breathable gas may be enriched with a therapeutic gas, such as oxygen, or include a therapeutic agent, and be in a variety of forms, such as a nebulized mist, powder or gas.

Figure 2:
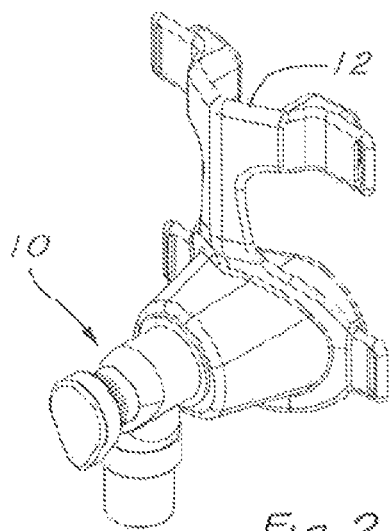
FIG. 2 is an isometric view of a nasal user interface which is coupled to the respiratory valve apparatus of FIG. 1.
Figure 3:
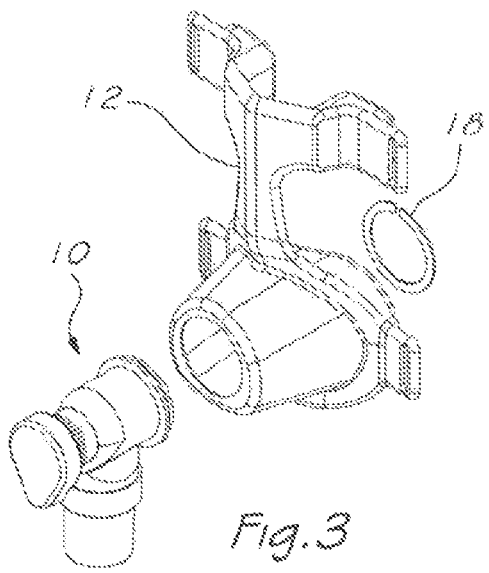
FIG. 3 is an exploded isometric view of the system shown in FIG. 2.

FIG. 2 shows the respiratory valve apparatus 10 installed in a nasal user interface or mask 12. FIG. 3 shows an exploded view of the assembly of FIG. 2 including a retaining clip 18 applicable to retain the apparatus 10 to the mask 12, although it will be appreciated by persons skilled in the art that the outlet port may feature shoulders, circlip retention grooves or alternate structural forms for retaining the valve apparatus 10 to the mask 12. Alternatively, the valve apparatus may be incorporated into the body of mask (FIGS. 40 to 43).

The respiratory valve apparatus 10 delivers a pressurised flow of breathable gas to the airway of the user, and may be used in conjunction with a user interface and (FIGS. 4 and 5) comprises a rigid valve body 20 which includes an inlet port 22 for continuously receiving breathable gas under pressure from the gas flow generator 14 or other ventilator device. There is an outlet port 24 which, via the mask 12, releases the breathable gas to the user's airway during an inhalation phase and receives exhaled gas during an exhalation phase of the user's respiratory cycle.

A breathable gas flow passage 34 (as shown by the path of the unbroken arrows in FIG. 6) communicates between the inlet port 22 and the outlet port 24. Additional elements such as the inlet swivel connector 76 and optional humidification element 61 may extend this passage. There is an exhaust port 28 for releasing the exhaled gas to atmosphere. Exhaust port 28 includes a plurality of circumferentially spaced exhaust apertures 30. An exhaled gas flow passage 36 (as shown by the path of the unbroken arrows in FIG. 7) communicates between the outlet port 24 and exhaust ports 28.

Figure 4:
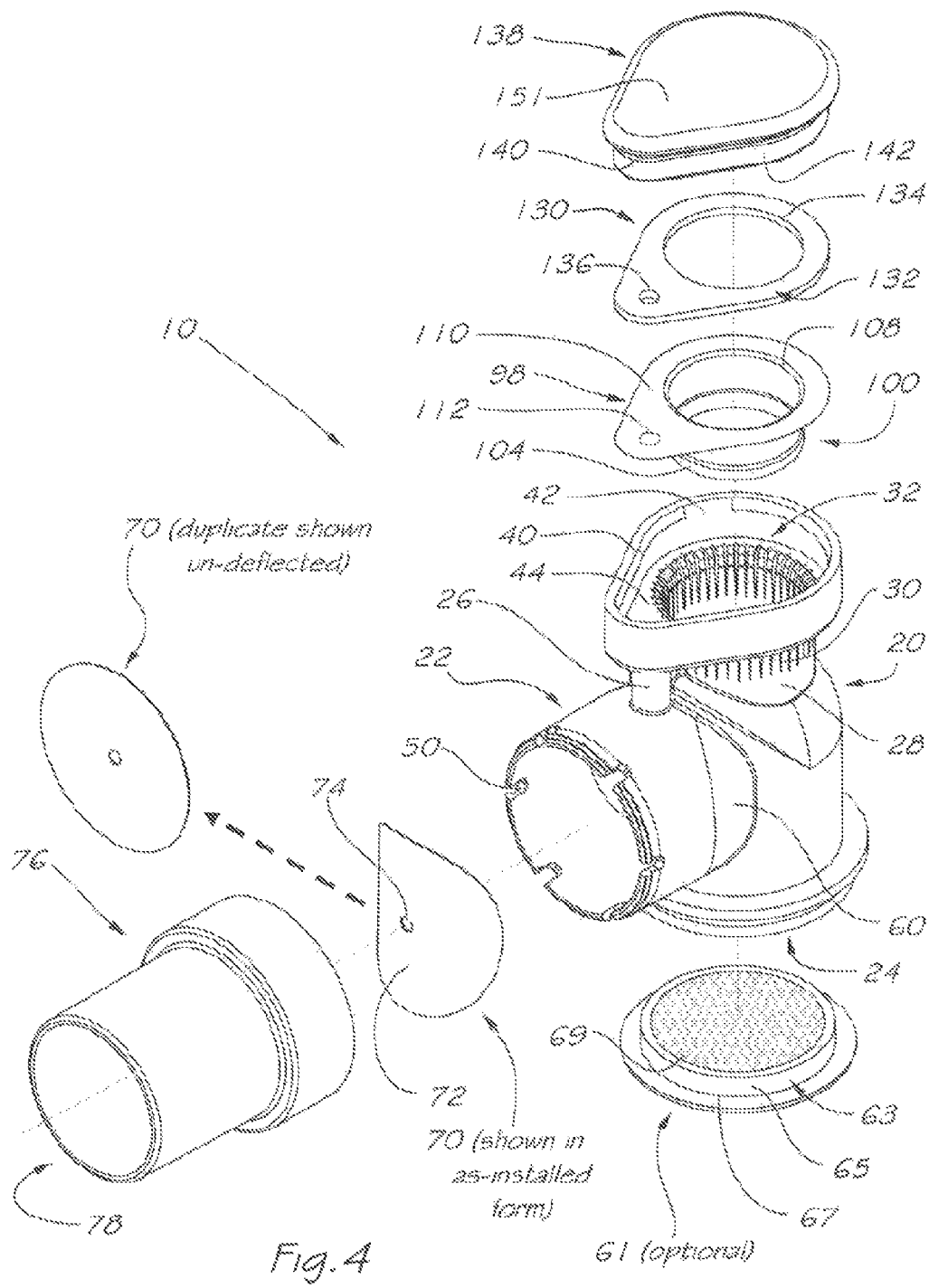
FIG. 4 is an exploded isometric view of the respiratory valve apparatus shown in FIGS. 1, 2 and 3.
Figure 5:
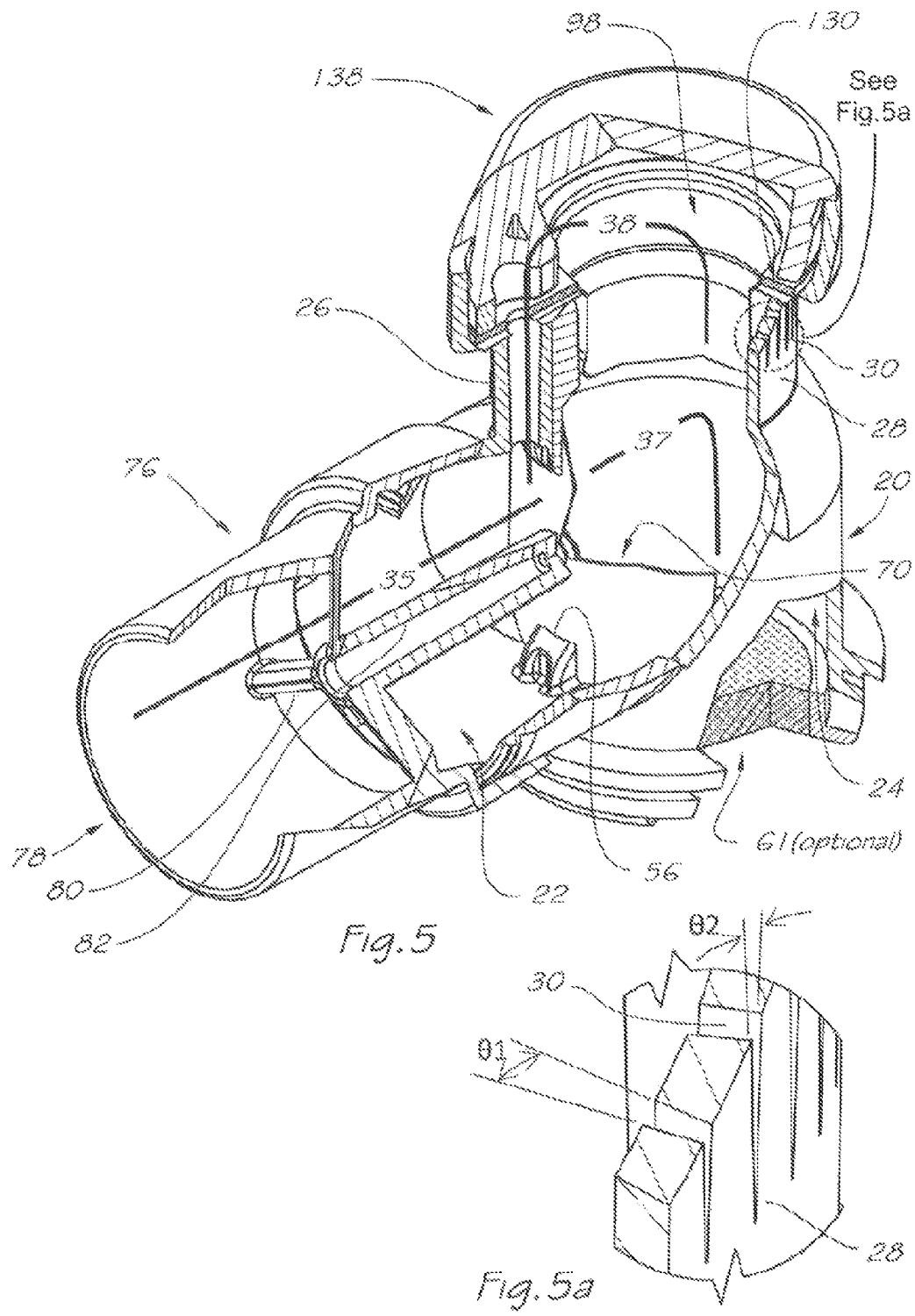
FIG. 5 is an isometric and partly cut-away view of the respiratory valve apparatus shown in FIG. 4 and showing a zone of detail for subsequent views.
Figure 9:
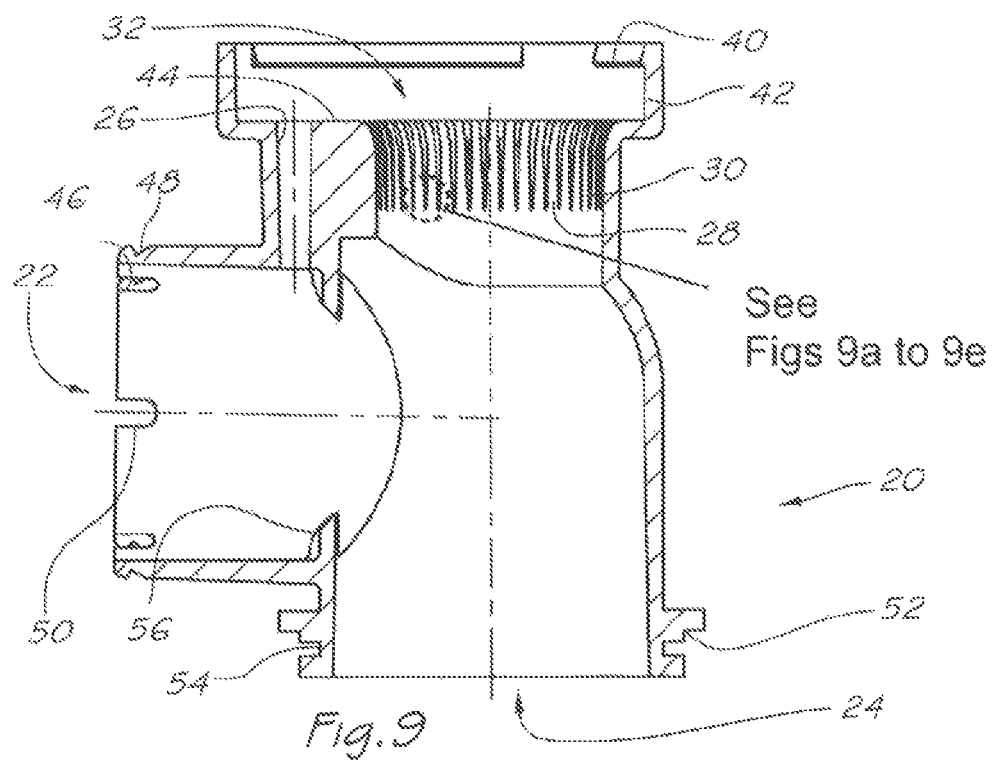
FIG. 9 is a sectional side view of the rigid valve body of FIG. 8 through plane A-A and showing a zone of detail for subsequent views.
Figure 10:
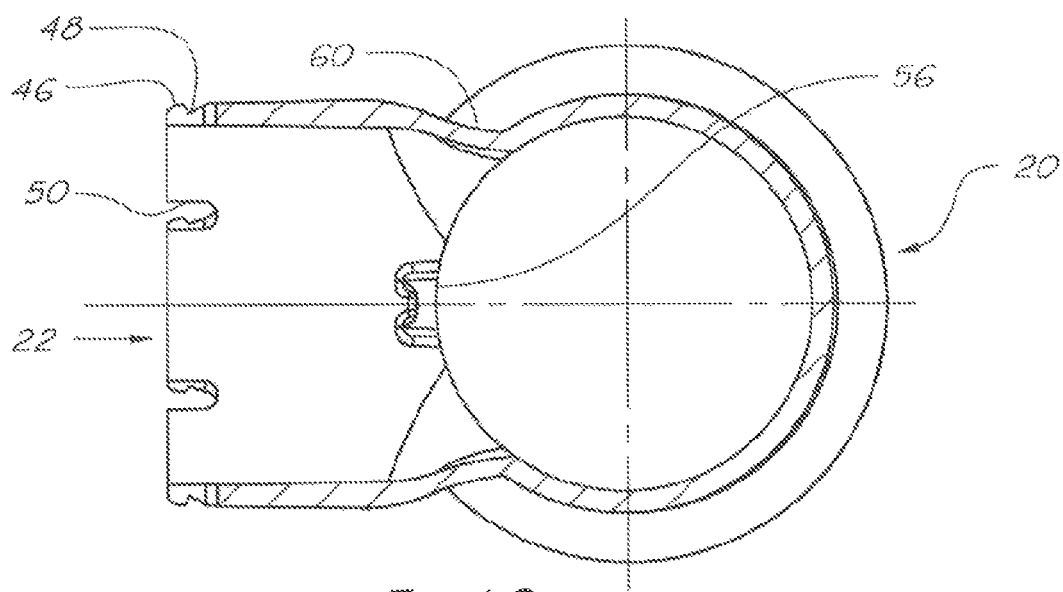
FIG. 10 is a sectional view of the rigid valve body of FIG. 8 through plane B-B.
Figure 16:
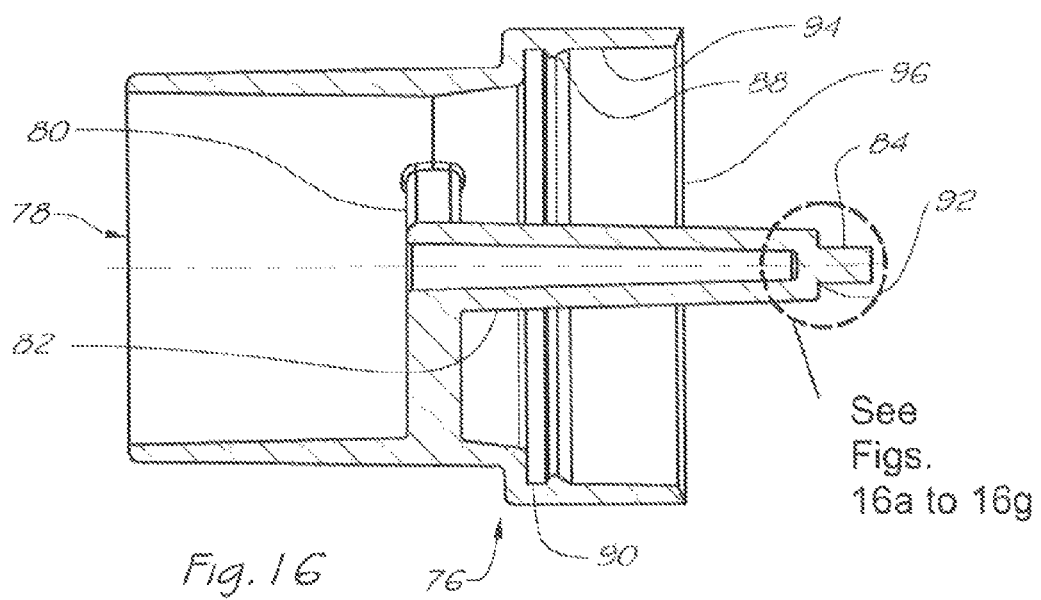
FIG. 16 is a sectional side view of the swivel connector of FIG. 15 through the section plane A-A and showing a. zone of detail for subsequent views.
Figure 16A:
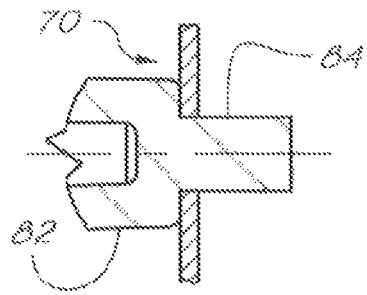
FIG. 16a is a detail view showing the installation of components to the swivel connector of FIG. 15.
Figure 16B:
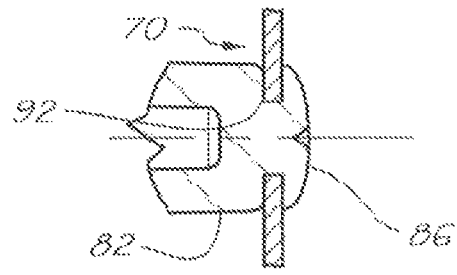
Figure 16C:
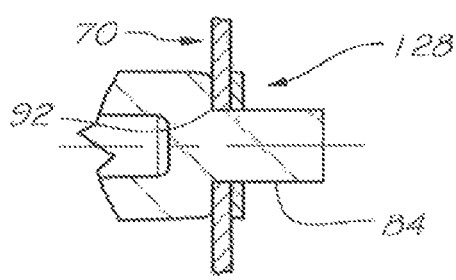
FIG. 16c is a detail view showing a further embodiment for the installation of components to the swivel connector of FIG. 15.
Figure 16D:
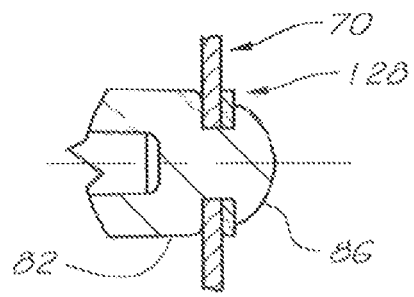
FIG. 16d is a detail view showing a deformation applied to the swivel-connector of FIG. 15 in order to fasten the components shown in FIG. 16c.
Figure 16E:
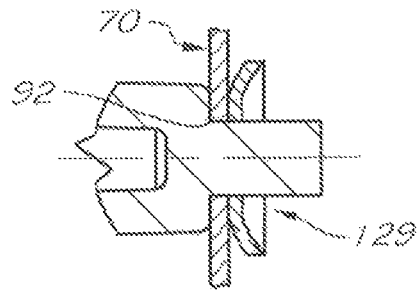
FIG. 16e is a detail view showing a further embodiment for the installation of components to the swivel connector of FIG. 15.
Figure 16F:
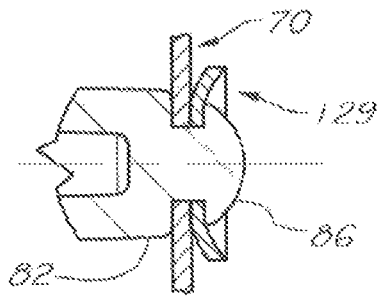
FIG. 16f is a detail view showing a deformation applied to the swivel connector of FIG. 15 in order to fasten the components shown in FIG. 16e.
Figure 16G:
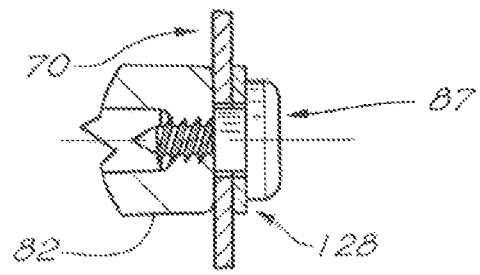
FIG. 16g is a detail view showing components installed to a swivel connector similar to that of FIG. 15 and retained by a separate fastener.

A first valve 70 is located in the breathable gas flow passage 34 and divides that to passage into an upstream portion 35 and a downstream portion 37. In this embodiment, the first valve 70 is a non-return or one-way valve. The non-return valve 70 comprises a flexible flap 72 (FIG. 4) which is weakly biased to a closed position under neutral differential pressure (as depicted in FIG. 5) and under greater differential pressure from inlet 78 is deflected into two halves about a generally vertical line (FIG. 6) to an opened position. Non-return valve 70 is retained by central hole 74 to the swivel connector 76 and locates on the shoulder 92 (FIG. 16) defined by central post 82 and mounting post 84 which is subsequently heat staked to form mushroom head 86 (FIGS. 16b-f). As would be apparent to one skilled in the art, many structural forms of retention are possible including placing the valve directly to the swivel 76 (FIGS. 16a to 16b), heat-staking with added flat washer(s) 128 (FIGS. 16c to 16d), heat-staking with added contoured washer(s) 129 (FIGS. 16e to 16f) or retention by an additional screw or fastening element 87 (FIG. 16g). Once installed on the swivel 76, the swivel and valve assembly may then be installed onto the inlet port 22 of the rigid valve body 20. Retention of the swivel 76 to the valve body 20 may be achieved by structural forms such as the elastic engagement of the rib 88 and groove 90 of the swivel 76 (FIG. 16) to the rib 46 and groove 48 of the valve body 20 (FIGS. 9, 10). Slots 50 may optionally be provided on the inlet port 22 in order to reduce the forces required to install the swivel 76 to the valve body 20.

If the valve 70 were to distort during operation into the inlet port 22, function of respiratory valve apparatus 10 would be impaired. To mitigate this circumstance, one or more stops 56 may be provided within the inlet port 22. Stops 56 have a ramp-like form in order to minimise resistance to insertion, but maximise resistance to withdrawal of valve 70 from rigid valve body 20.

Figure 14:
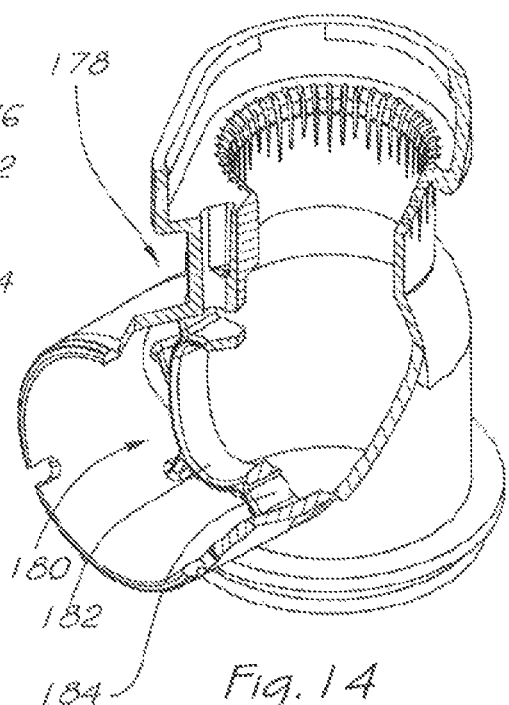
FIG. 14 is an isometric and partly cut-away view of a third embodiment of the rigid valve body of the respiratory apparatus and featuring a grating to mitigate undesired deflection modes of the inlet valve.
Figure 15:
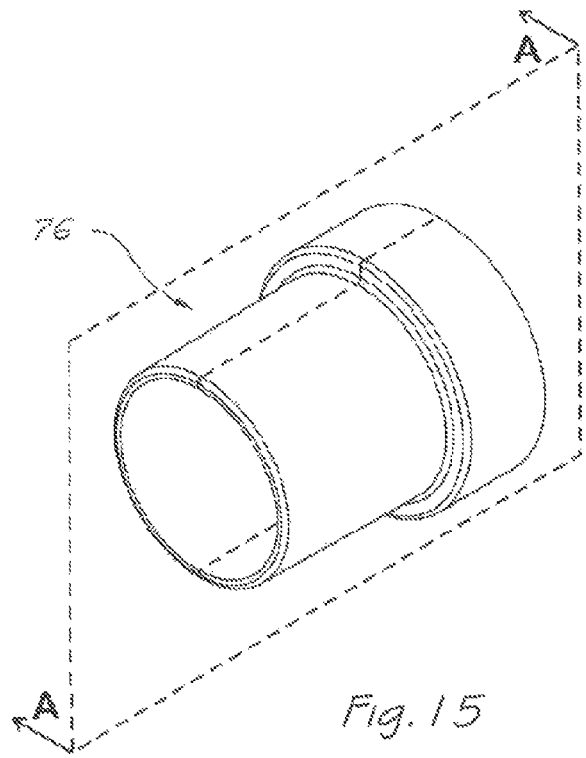
FIG. 15 is an isometric view of the swivel connector of the respiratory valve apparatus of FIG. 4 and showing a vertical section plane A-A.

Other structural forms of stop are shown in FIG. 14 attached to rigid valve body 178 comprising a grating 180, which includes a large aperture 182 through which valve 70 is passed during installation, and a plurality of webs 184 supporting aperture 182.

It will be appreciated by skilled persons in the art that the non-return valve 70 may take alternate structural forms that are all weakly biased to a closed position.

The non-return valve 70 will open under pressure of breathable gas received through the inlet swivel connector 76 and then through the inlet port 22 during the inhalation phase (FIG. 6), and so permit flow of breathable gas to the user, and will close under pressure of exhaled gas received through the outlet port 24 during the exhalation phase (FIG. 7), despite the maintenance of a pressurised flow of breathable gas through the inlet port 22 during the exhalation phase.

By the closing of the non-return valve 70, the exhaled gas received through the outlet port 24 is prevented from exiting through the inlet port 22, but flows through the exhaled gas flow passage 36.

As shown in FIGS. 4, 5, 6 and 7, an optional heat and moisture exchange (HME) element 61 may be added to the outlet port 24. The HME element 61 comprises a housing 63 with an HME insert 69 preferably constructed from an open cell foam treated with a hygroscopic material such as calcium chloride or material with similar hygroscopic properties, or a hydrophobic filter material as described in the prior art. Choice of material will be dependent on efficiency of capture and release of heat and moisture and resistance to gas flow. Insert 69 may optionally be treated with anti-bacterial agents to mitigate colonisation of the insert by microbes. Absorbed heat and condensation would be available for release back into breathable gas flow passage 34 and thence into the user's airway to reduce drying thereof. Annular housing 63 comprises a cylindrical body 65 and shoulder 67 adapted to locate and sealably retain humidification element 61 to outlet port 24. It will be appreciated by those skilled in the art that whilst the form of the housing in this case is cylindrical, its form would be tailored to match that of the outlet port be it cylindrical, oval or other suitable cross section. Additionally, both the retention of housing 63 by outlet port 24 and humidification element 61 by housing 63 may be by frictional means as depicted or alternatively by positive means such as screw thread, barbs, bayonet, adhesive or other suitable means apparent to those skilled in the art.

Figure 6:
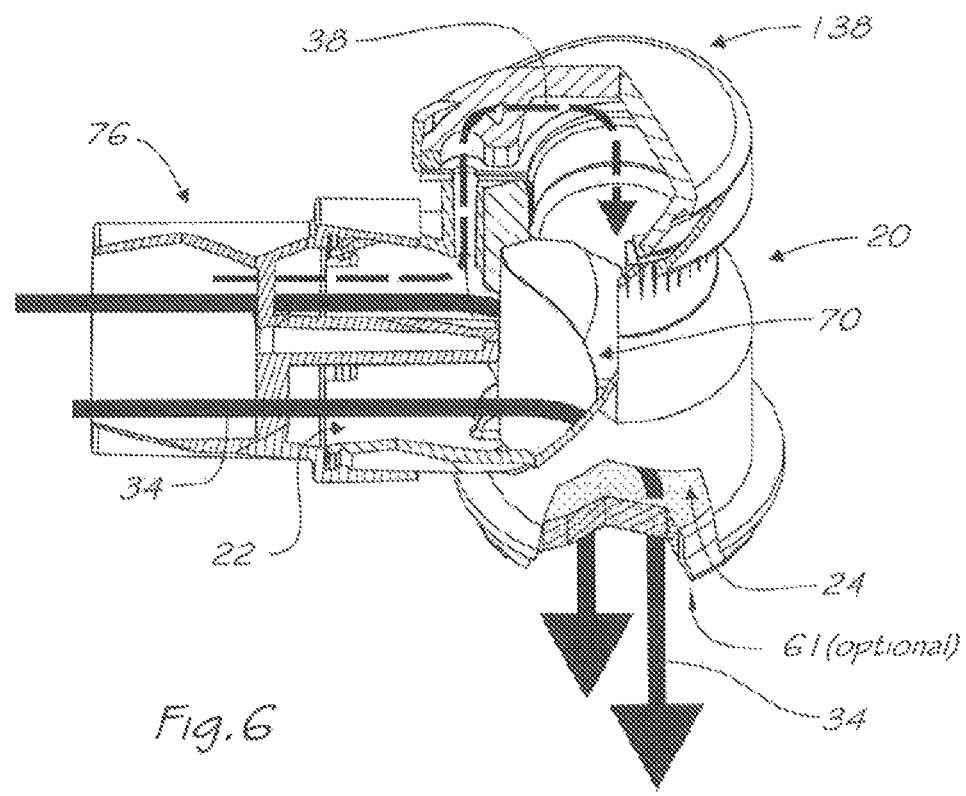
FIG. 6 is a pictorial and partly cut-away view of the respiratory valve apparatus of FIG. 4, showing the path of breathable gas during an inhalation phase.
Figure 7:
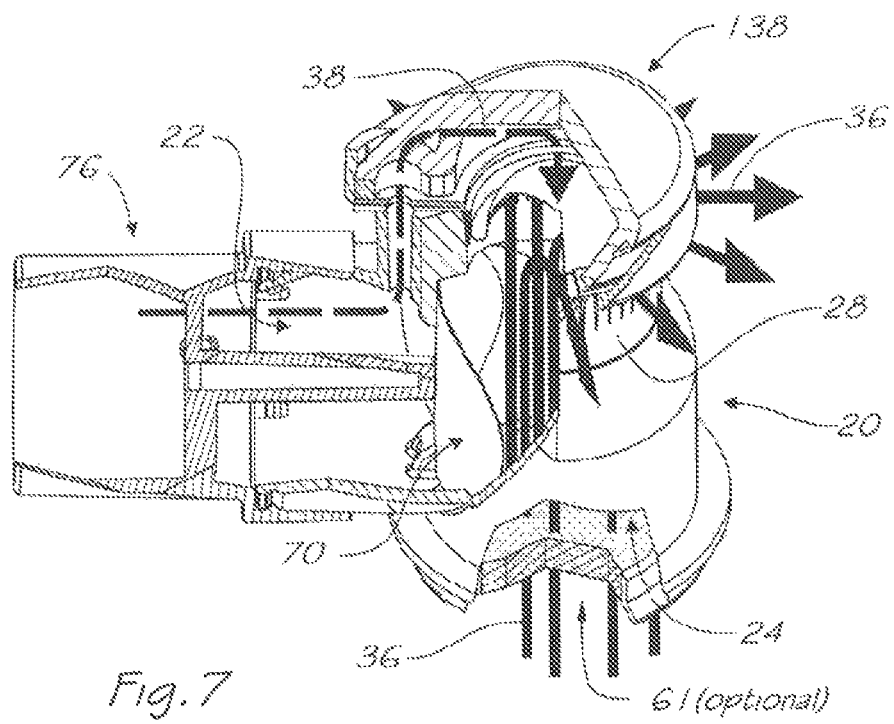
FIG. 7 is a pictorial and partly cut-away view of the respiratory valve apparatus of FIG. 4, showing the path of breathable gas during an exhalation phase.
Figure 8:
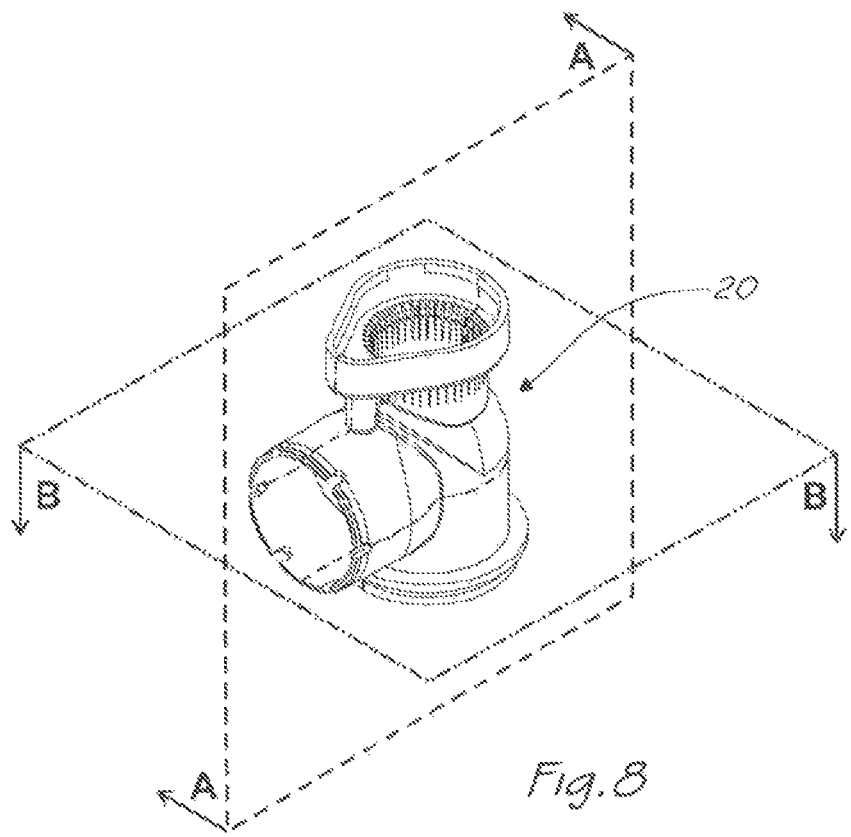
FIG. 8 is an isometric view of a first embodiment of a rigid valve body of the valve apparatus of FIG. 4 and showing vertical section plane A-A and near horizontal section plane B-B which passes through the centre line of the inlet port of the aforementioned valve body.
Figure 11:
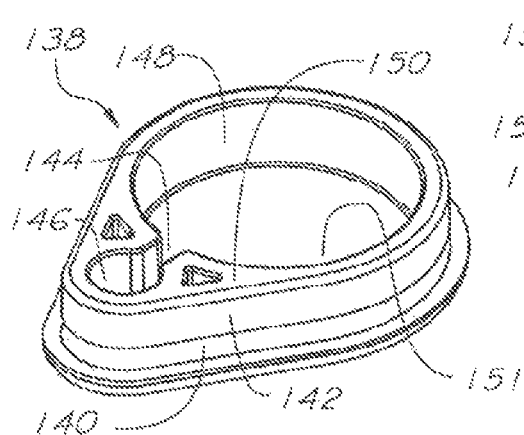
FIG. 11 is an isometric view of the cap of the respiratory valve apparatus of FIG. 4.
Figure 17:
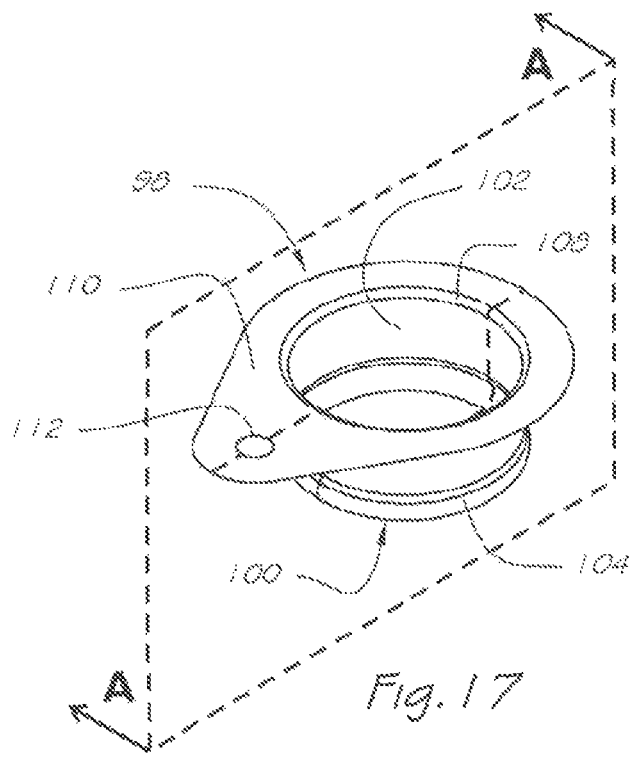
FIG. 17 is an isometric view of the balanced pressure valve of the respiratory valve apparatus of FIG. 4 and showing a vertical sectional plane A-A.
Figure 18:
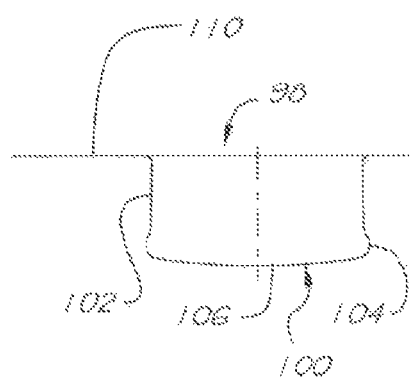
FIG. 18 is a sectional side view of the balanced pressure valve of FIG. 17 through section plane A-A.

A second valve 98 is located in exhaled gas flow passage 36 and, in this embodiment, is a balanced pressure valve. Balanced pressure valve 98 (FIGS. 17 to 18) comprises a flexible membrane 100, which is weakly biased to an expanded position where it closes the exhaust apertures 30 under ambient or neutral pressure (as shown in FIG. 5) and under pressure of breathable gas received through the inlet port 22 during the inhalation phase (FIG. 6). Balanced pressure valve 98 further comprises a flange portion 110 which is sealably retained between the valve receptacle 32 of the valve body 20 (FIGS. 4, 5) and the compression rim 150 of the cap 138 and optionally with spacing gasket 130 (FIGS. 4, 5, 11). A hole 112 (FIGS. 4 and 17) provides continuity of breathable gas equilibrium passage 38 (FIG. 5) which passes through it and corresponding holes 136 and 134 in gasket 130. Flexible membrane 100 of balanced pressure valve 98 includes a main body portion 102 of generally cylindrical form and preferably forming an expanding taper towards an expanded annular sealing portion 104 and closed first end 106 at its base, and an open second end 108 at the junction between the flanged portion 110 and main body portion 102.

Cap 138 (FIGS. 4, 11) includes a wall 142 which locates within the corresponding peripheral wall 42 of the valve receptacle 32 of the valve body 20, and is retained thereto by engagement of the fastening rib 40 (which may optionally be either continuous, or broken as shown for lower installation forces) with the groove 140 of the wall 142. Chambers 146 and 148 linked by channel 144 effect continuity of the breathable gas equilibrium passage 38.

The flexible membrane 100 will, under pressure of exhaled gas flowing through the exhaled gas flow passage 36 during the exhalation phase (FIG. 7), flexibly deform to a semi or fully collapsed position so as to open the exhaust apertures 30, whereby the exhaled gas is released to atmosphere.

The exhaust apertures 30 (FIG. 5a) are generally tapered longitudinally by angle $\Theta 2$, which is at least large enough to accommodate tooling draft and through transverse section may comprise a contracting taper $\Theta 1$ to enhance noise reduction by the emitted jet of air.

Although any suitable width of the exhaust apertures may be selected it will preferably be in the range 0.2 to 1 mm at their widest part to mitigate noise of exhausting gas, and provide a total area including all apertures open to the exterior preferably in the range 50 to 200 square mm with embodiments manufactured with aperture areas to suit a particular rate of exhaust flow and hence clinical application.

Figures 9A, 9B, 9C:
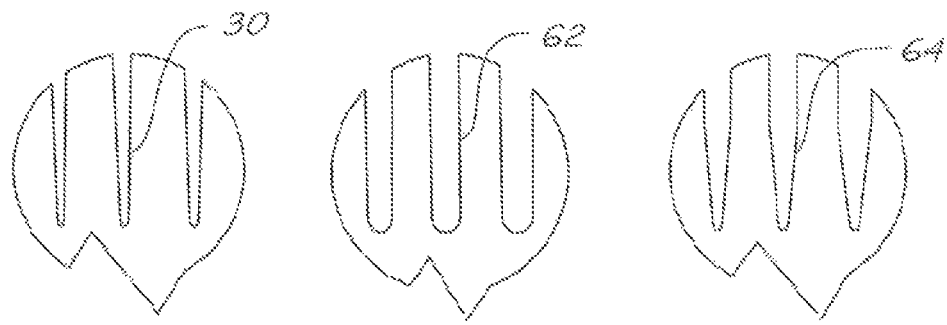
FIGS. 9a to 9e are enlarged views of alternative embodiments of the exhaust apertures highlighted in FIG. 9.
Figures 9D, 9E:
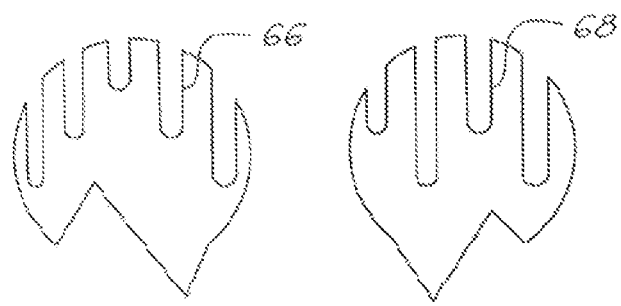

The converging end geometry of the exhaust apertures 30 may optionally comprise a variety of forms as shown in FIGS. 9a to 9e. Dramatic contractions towards the ends of the apertures as shown in FIGS. 9a and 9c and staggered end geometries shown in FIGS. 9d and 9e further accentuate the rate of increase in exhaust aperture area revealed in relation to displacements of the flexible membrane 100. Contraction and stagger produces small airflows at small displacements of the membrane 100 and proportionally increasing airflows as membrane displacement advances to uncover greater aperture area. This further achieves a cushioning effect as the user transitions from exhalation to inhalation, mitigating the tendency for sudden transitional tensioning of the membrane during early phase exhalation and the corresponding pulsing sensation produced thereby which would otherwise be experienced with uniform aperture end geometry such as shown in FIG. 9b. It will be apparent to those skilled in the art that the end geometries shown here may be used singularly or in combination and that these represent a sample of possible options to achieve the performance goals described.

Figure 19:
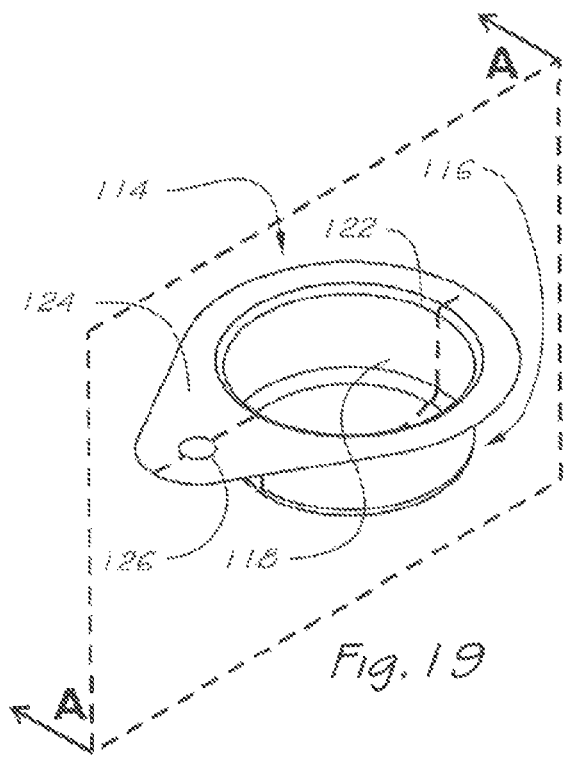
FIG. 19 is an isometric view of a second embodiment of the balanced pressure valve of the respiratory valve apparatus of FIG. 4 and showing a vertical sectional plane A-A.
Figure 20:
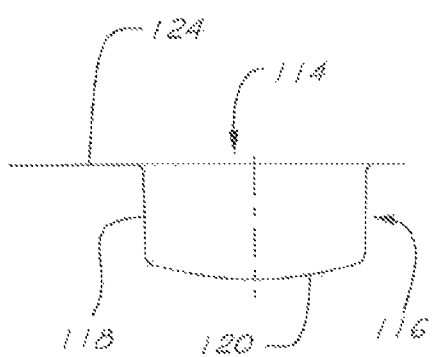
FIG. 20 is a sectional side view of the balanced pressure valve of FIG. 19 through section plane A-A.

In an alternative embodiment (FIGS. 19 and 20), balanced valve 114 features a similar flanged portion 124, although it includes a flexible membrane 116 having a generally cylindrical main body portion 118 and preferably forming a converging taper towards a closed first end 120 at its base, and an open second end 122 at the junction between the flanged portion 124 and main body portion 118 which sealably conforms against the inside of the exhaust port 28 of the valve body 20.

Membrane 100 and 116 of balanced valves 98 and 114 are preferably manufactured from flexible polyethylene film with thickness less than 50 micrometres and preferably, in the range 2 to 10 micrometres and manufactured by vacuum forming, although other manufacturing techniques may be deployed. This combination of material and thickness emphasizes flexibility over elasticity such that any increase in the effort of breathing caused by membrane stiffness is minimized. This is particularly significant in continuous positive pressure treatment where it is preferred to limit pressure increases on exhalation above source pressure wherein balanced valve 98 or 114 in combination with area of exhaust port 28 and individual apertures 30 is designed to limit exhalation pressure swing during breathing to less than 2 cm of water. and preferably to less than 0.5 cm of water.

Figure 12:
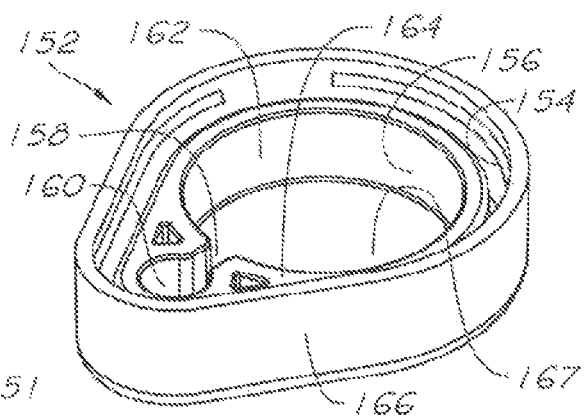
FIG. 12 is an isometric view of a second embodiment of the cap for the respiratory valve apparatus.
Figure 13:
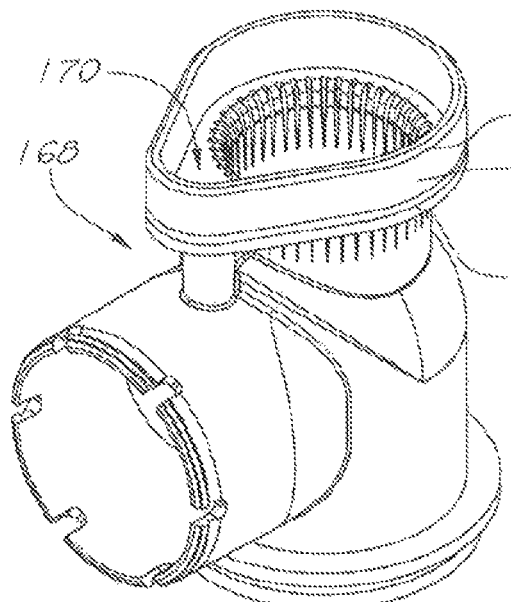
FIG. 13 is an isometric view of a second embodiment of the rigid valve body of the respiratory apparatus and adapted to receive the cap of FIG. 12.

In an alternative embodiment (FIGS. 12, 13), the cap 152 now includes an external peripheral wall 166 which envelopes corresponding wall 172 of valve body 168. Retention is achieved by engagement of the internal fastening rib 154 of the cap 152 within the corresponding groove 174 of the valve body 168 and a chamfer or ramp 176 may be provided to facilitate smooth engagement thereby.

Another embodiment of a respiratory valve apparatus according to the present invention is shown in FIGS. 21 to 24. Respiratory valve apparatus 282 delivers a pressurised flow Of breathable gas to the airway of a user, and comprises a rigid valve body 288 which includes an inlet port 290 for continuously receiving breathable gas under pressure from a pressure source or gas flow generator. There is an outlet port 292 which, via a mask, releases the breathable gas to the user's airway during an inhalation phase and receives exhaled gas during an exhalation phase of the user's respiratory cycle. A breathable gas flow passage 294 (as shown by the path of the unbroken arrows in FIG. 23) communicates between the inlet port 290 and the outlet port 292.

There is an exhaust port 296 for releasing the exhaled gas to atmosphere. The exhaust port 296 includes a plurality of circumferentially spaced apart exhaust apertures 298.

An exhaled gas flow passage 300 (as shown by the path of the unbroken arrows in FIG. 24) communicates between the outlet port 292 and the exhaust port 296.

A first valve 302 is located in the passage 294 and divides that passage into an upstream portion 306 and a downstream portion 308. The first valve 302 is a nonreturn valve. Rigid valve body 288 has a valve receptacle 310 comprising a peripheral sealing rim 314, a mounting bar 316 which vertically and symmetrically bridges passage 294 at the junction of the upstream and downstream portions 306, 308. Mounting bar 316 has in a central position, a keyed mounting hole 318 adapted to engage in a fixed orientation the keyed stem 322 and barb 320 of non-return valve 302. Non-return valve 302 comprises a flexible flap 312 which is weakly biased to a closed position under ambient pressure and which sealably engages peripheral sealing rim 314 during exhalation and, when in an opened position, is pivotally deflected into two halves about a line or lines aligned with mounting bar 316. Nonreturn valve 302 may optionally have provided on its rear face a groove or grooves 304 which provide a line or lines of reduced stiffness and correspondingly facilitate more pronounced deflection about these lines.

The non-return valve 302 will open under pressure of breathable gas received through the inlet port 290 during the inhalation phase (FIG. 23), and so permit, flow of breathable gas to the user, and will close under pressure of exhaled gas received through the outlet port 292 during the exhalation phase (FIG. 24), despite the maintenance of a pressurised flow of breathable gas through the inlet port 290 during the exhalation phase.

Figure 23:
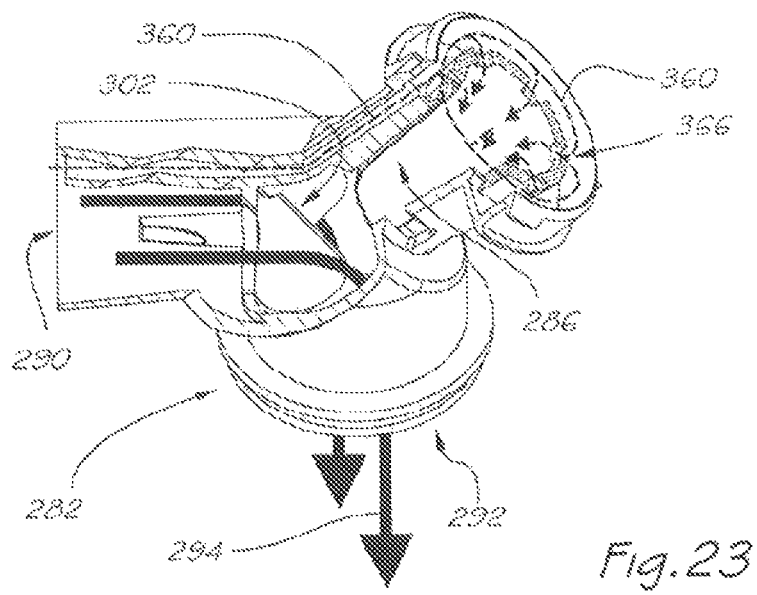
FIG. 23 is a pictorial and partly cut-away view of the respiratory valve apparatus of FIG. 21 in which the end cap is omitted for viewing clarity, and further showing the path of breathable gas during an inhalation phase.
Figure 24:
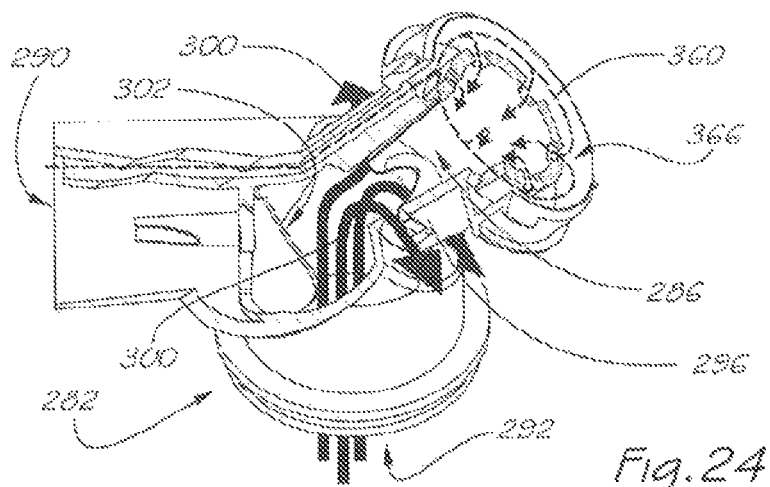
FIG. 24 is a similar view to that of FIG. 23, and further showing the path of exhaled gas during an exhalation phase.
Figure 27:
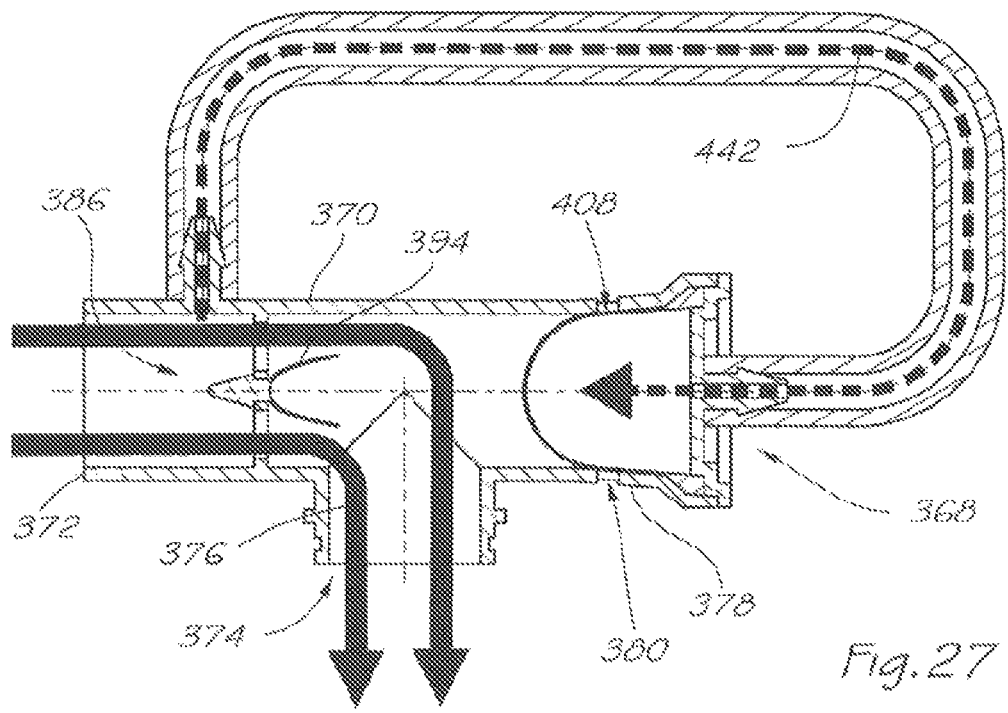
FIG. 27 is a similar view to that of FIG. 26, and further showing the path of breathable gas during an inhalation phase.
Figure 28:
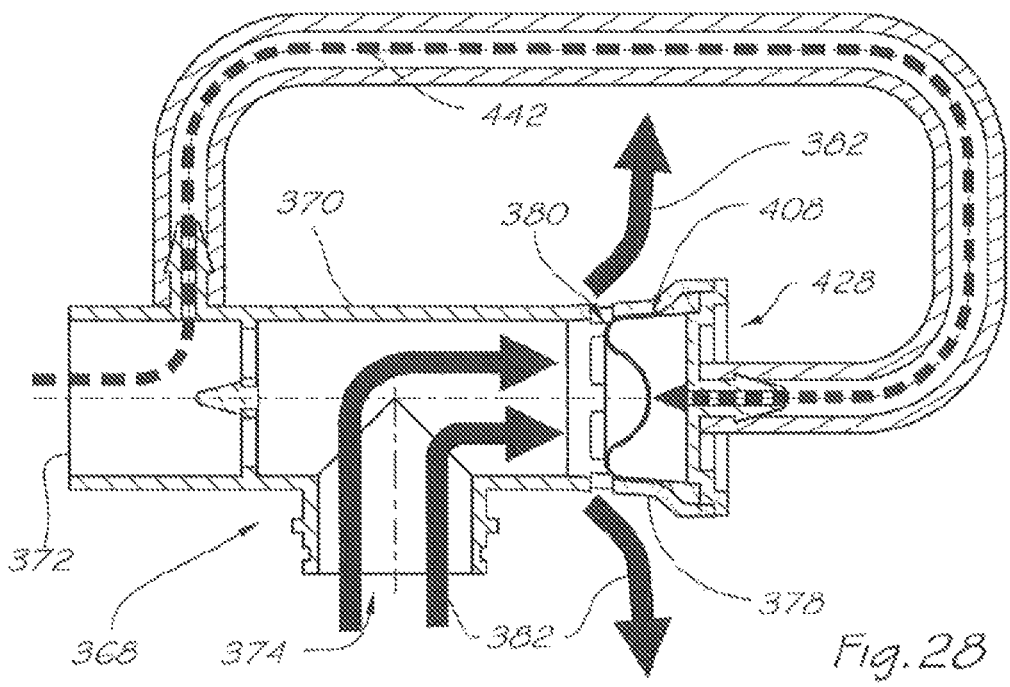
FIG. 28 is a similar view to that of FIG. 26, and further showing the path of exhaled gas during an exhalation phase.
Figure 36:
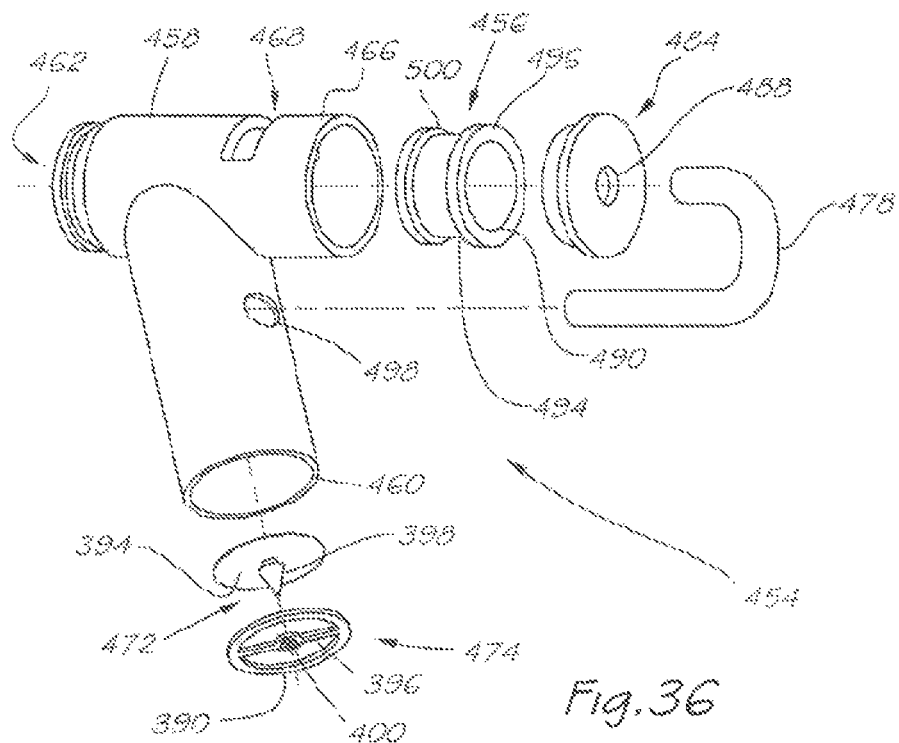
FIG. 36 is a pictorial exploded view of the respiratory valve apparatus according to a second aspect of the present invention.

By the closing of the non-return valve 302, the exhaled gas received through the outlet port 292 is prevented from exiting through the inlet port 290, but flows through the exhaled gas flow passage 300 (FIG. 24). A second valve 328 is located in the exhaled gas flow passage 300 and is a balanced pressure valve. Balanced pressure valve 328 is similar in function to balanced pressure valve 98 (FIG. 17, 18) and similarly comprises a flexible membrane 284 which has a sock-like structure defining an internal cavity 286, and has a generally cylindrical main body portion 324, the outer surface of which corresponds to the inner wall of the valve body against which it seals circumferentially, a closed first end 326 which is preferably hemispherical and an open second end 330, whereby operation of the valve controls the opening and closing of the exhaust apertures 298 that are circumferentially spaced apart along a wall of the valve body. The flexible membrane 284 is weakly biased to an expanded position where it closes exhaust apertures 298 under ambient pressure and under pressure of breathable gas received through the inlet port 290 during the inhalation phase (FIG. 23). The flexible membrane 284 will, under pressure of exhaled gas flowing through the exhaled gas flow passage 300 during the exhalation phase, flexibly deform to a collapsed position so as to open the exhaust apertures 298, whereby the exhaled gas is released to atmosphere (FIG. 24). Balanced pressure valve 328 is preferably manufactured from a moldable elastomer such as liquid silicone rubber with thickness typically less than 100 micrometres, although greater thickness may be used depending on the application.

The flexible membrane 284 has a retaining flange 332 by which it is fitted circumferentially against the wall of the exhaust port 296 of the valve body 288. The retaining flange 332 has an outermost downward lip 334 which engages around uppermost shoulder segments 336 of a collar portion 338 of the exhaust port 296. The retaining flange 332 also has a lowermost groove 318 which engages around an inner ridge 340 of the collar portion 338. A retaining cap 342 is engaged around the retaining flange 332, such that the retaining flange 332 is sandwiched between the upper retaining cap 342 and the lower collar portion 338. The retaining cap 342 is optionally aligned with the collar portion 338 by notches 344 formed in the side wall 348 of the cap 342 which engage optional protrusions 350 formed on the side wall 352 of the collar portion 338. The side wall of the retaining flange 332 has one or more bias pressure 10 flow holes 356, and the side wall 348 of the retaining cap 342 has locking slots 358 for receiving there through respective shoulder segments 336 of the collar portion 338 when the retaining flange 332 is sandwiched between the upper retaining cap 342 and the lower collar portion 338 of the exhaust port 296. Retaining cap 342 may optionally have a locating boss 346 which when assembled, projects downwards into the open second end 330 of balanced pressure valve 328 and thereby effecting more positive engagement of the valve 328.

The respiratory valve apparatus 282 also includes breathable gas equilibrium passage 360 (as shown by the path of the broken arrows in FIGS. 23 and 24) defined by a bias pressure tube 362, which is in gas flow communication between the inlet port 290 and the exhaust port 296. The bias pressure tube 362 is formed integrally with the valve body 288, being internal of the body at the inlet port 290 but external of the exhaust port 296.

To accommodate the flexible flap 312 of the non-return valve 302' within the partly internally obstructed inlet port 290, flexible flap 312 has a cut-out portion 364 in the outer shape of the bias pressure tube 362 so as to maintain a generally air-tight barrier between the upstream and downstream portions 306, 308 of the passage 294 when the non-return valve is in a closed position.

The end opening of the bias pressure tube 362 in the exhaust port 296 opens out into a circular passage 366 between the side wall 352 of the collar portion 338 and the side wall 354 of the retaining flange 332, which is a sealed annular space except for the bias pressure flow holes 356 in the side wall 354 leading to the internal cavity 286 defined by the sock-like structure of the flexible membrane 284.

During the inhalation phase, when a pressurised flow of breathable gas is delivered into the valve body 288 through the inlet port 290, a volume of breathable gas is diverted into. and is maintained within, the breathable gas equilibrium passage 360, and hence within the internal cavity 286 of the flexible membrane 284, at an equilibrium pressure sufficient to maintain the flexible membrane 284 in an expanded position where it closes the exhaust apertures 298, despite a larger volume of breathable gas flowing through the breathable gas flow passage 294.

Figure 22:
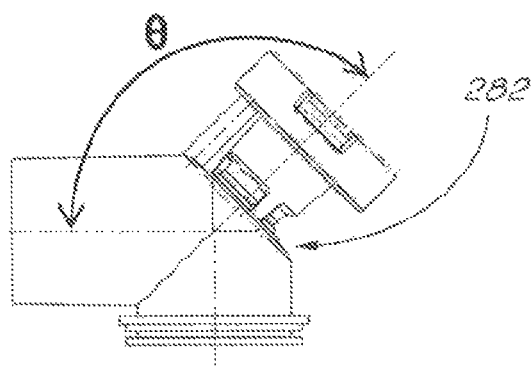
FIG. 22 is a side view of the respiratory valve apparatus of FIG. 21.

During the exhalation phase, when the non-return valve 302 is forced to close by the greater pressure of the exhaled gas within the downstream portion 308 of the passage 294 than the pressure of the breathable gas entering the inlet port 290, the pressure of exhaled gas within the exhaled gas flow passage 300 is sufficiently greater than the equilibrium pressure of the breathable gas maintained within the internal cavity 286 of the flexible membrane 284 to cause the flexible membrane 284 to flexibly deform to a collapsed position and thereby open the exhaust apertures 298 so as to permit release of the exhaled gas to atmosphere. FIG. 22 shows a side view of respiratory valve apparatus 282 indicating that alternate configurations are possible where the angular orientation Θ of the exhaust port 296 to the horizontal may vary, preferably between 90° and 180°. It will be apparent to those skilled in the art that the potential for corresponding angular variations between the inlet port and exhaust port may be applicable to prior and subsequent embodiments in this application.

It can be appreciated that while exhaust apertures 298 in the respiratory valve apparatus of FIGS. 21 to 24 are shown circumferentially around exhaust port 296 they may also be configured as depicted in the first aspect of the invention, namely they may embody longitudinal slots as shown in FIGS. 9, 9a-e and as previously described.

Another embodiment of a respiratory valve apparatus according to the present invention is shown in FIGS. 25 to 28.

The respiratory valve apparatus 368 delivers a pressurised flow of breathable gas to the airway of the user, and comprises a rigid valve body 370 which includes an inlet port 372 for continuously receiving breathable gas under pressure from the gas flow generator 14 or other ventilator device. There is an outlet port 374 which, via the mask 12, releases the breathable gas to the user's airway during an inhalation phase and receives exhaled gas during an exhalation phase of the user's respiratory cycle.

A breathable gas flow passage 376 (as shown by the path of the unbroken arrows in FIG. 27) communicates between the inlet port 372 and the outlet port 374.

There is an exhaust port 378 for releasing the exhaled gas to atmosphere. The exhaust port 378 includes a plurality of circumferentially spaced apart exhaust apertures 380. An exhaled gas flow passage 382 (as shown by the path of the unbroken arrows in FIG. 28) communicates between the outlet port 374 and the exhaust port 378.

A first valve 386 is located in the passage 376 and divides that passage into an upstream portion 388 and a downstream portion 392. In this embodiment, the first valve 386 is a non-return or one-way valve. The non-return valve 386 comprises a flexible flap 394 which is weakly biased to a closed position under ambient pressure (FIG. 26) and, when in an opened position, is deflected into two halves about a central line defined by a mounting bar 396. The non-return valve 386 is retained in a receptacle 384 comprising a peripheral sealing rim 390, a mounting bar 396 which symmetrically bridges the passage 376 at the junction of the upstream and downstream portions 388, 392, and a central mounting hole 400. Retention of the valve 386 in the receptacle 384 is accomplished by insertion of the barb 398 into the central mounting hole 400. In a closed position the flexible membrane 394 of valve 386 sealably engages the peripheral sealing rim 390 of the receptacle 384.

It will be appreciated by skilled persons in the art that the non-return valve 386 may take alternate structural forms that are all weakly biased to a closed position.

The non-return valve 386 will open under pressure of breathable gas received through the inlet port 372 during the inhalation phase (FIG. 27), and so permit flow of breathable gas to the user, and will close under pressure of exhaled gas received through the outlet port 374 during the exhalation phase (FIG. 28), despite the maintenance of a pressurised flow of breathable gas through the inlet port 372 during the exhalation phase.

By the closing of the non-return valve 386, the exhaled gas received through the outlet port 374 is prevented from exiting through the inlet port 372, but flows through the exhaled gas flow passage 382.

A second valve 404 is located in the passage 382 and, in this embodiment, is a balanced pressure valve. The balanced pressure valve 404 comprises a flexible membrane 408 which is weakly biased to an expanded position where it closes the exhaust apertures 380 under ambient pressure (FIG. 26) and under pressure of breathable gas received through the inlet port 372 during the inhalation phase (FIG. 27) and a flange portion 430 which is sealably retained between the mounting shoulder 402 of the exhaust port 378 and the flanged portion 424 of the barbed end cap 428. The flexible membrane 408 will, under pressure of exhaled gas flowing through the exhaled gas flow passage 382 during the exhalation phase (FIG. 28), flexibly deform to a collapsed position so as to open the exhaust apertures 380, whereby the exhaled gas is released to atmosphere.

Figure 21:
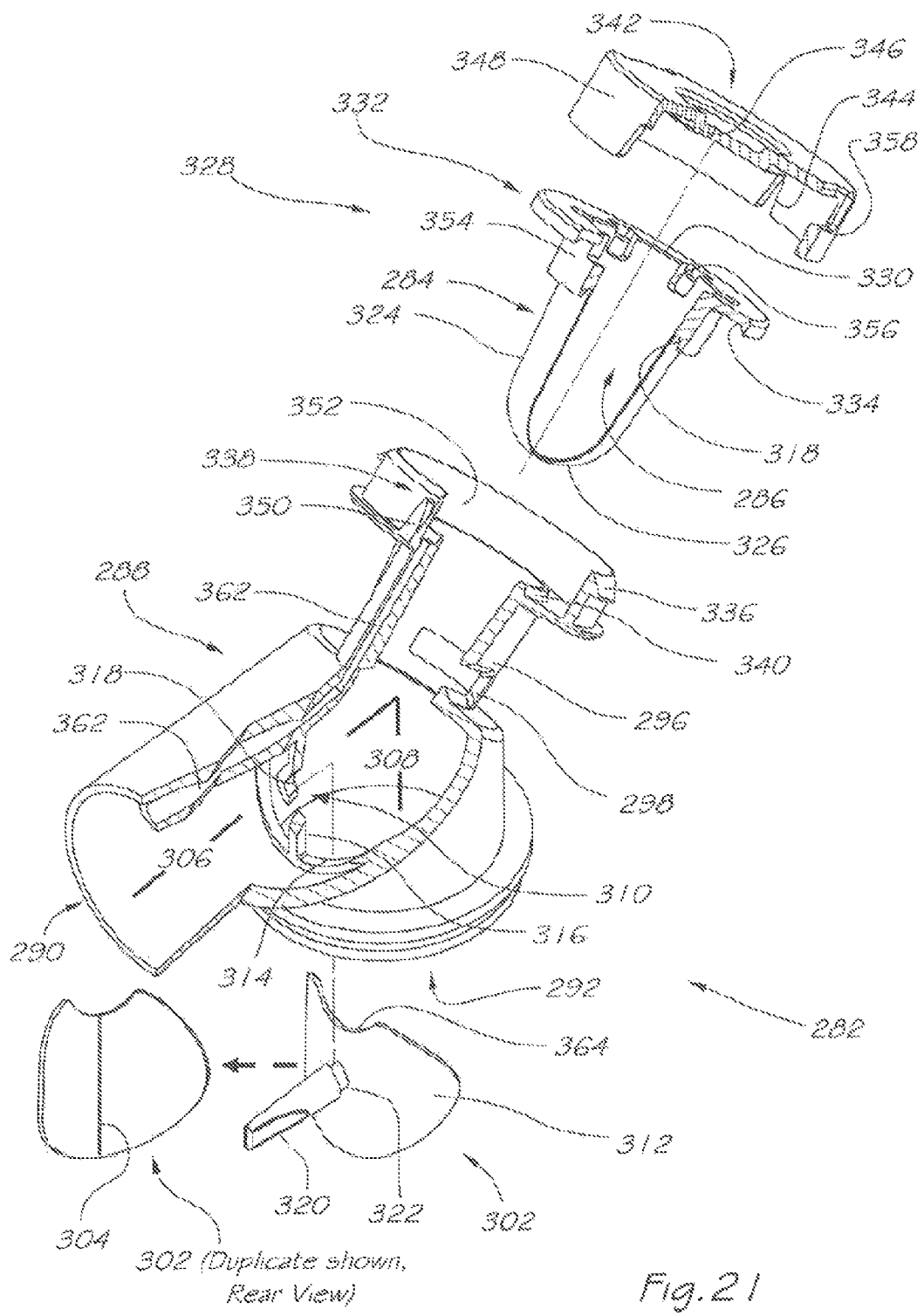
FIG. 21 is an isometric exploded and partly cut-away view of a respiratory valve apparatus according to a second embodiment of the present invention.

In this embodiment of the balanced pressure valve, and in the embodiments shown in FIGS. 29 to 32 and FIG. 35, the flexible membrane 408 (as specifically shown in FIG. 29) has a sock-like structure defining an internal cavity 412, and comprises a main body portion 414, the outer surface of which corresponds to the preferably generally cylindrical inner wall of the valve body against which it seals circumferentially, a closed first end 41 6 which is preferably hemispherical and an open second end 420, whereby operation of the valve controls the opening and closing of the exhaust apertures 380 that are circumferentially spaced apart along a wall of the exhaust port 378 of the valve body. It is further apparent that flexible membrane 408 may also be tapered in shape as shown in FIGS. 29 and 31 with the membrane becoming progressively smaller in circumference from the open end 420 to the closed end 416. Alternatively the sock-like structure is tapered in shape with the flexible membrane becoming progressively larger in circumference from its open end to its closed end, as suggested at 315 in FIG. 31. Flexible membrane 408 of balanced pressure valve 404 is similar in structure and function to flexible membrane 284 of balanced pressure valve 328 (FIGS. 21, 23 and 24). Balanced pressure valve 404 is likewise preferably molded from an elastomer such as silicone.

Another embodiment of the flexible membrane used in the balanced pressure valve is shown in FIG. 30. Balanced pressure valve 406 is similar in structure and function to balanced pressure valve 404, and like features which have like structure and function are identified with like numbers. Balanced pressure valve 406 differs from balanced pressure valve 404 in that it has a closed first end 418 which is more planar than hemispherical.

Another embodiment of the flexible membrane used in the balanced pressure valve is shown in FIG. 31. Balanced pressure valve 434 is similar in structure and function to balanced pressure valve 404, and like features which have like structure and function are identified with like numbers. Balanced pressure valve 434 differs from balanced pressure valve 404 in that it has an inner lining 432 or layer formed from a viscoelastic material or other material whose mechanical properties will dampen membrane vibration or minimise fluttering instabilities in the motion of the flexible membrane, without interfering with the operation of the flexible membrane in response to varying pressures. The flexible membranes of valves 404 and 434 are each connected to a flange portion 430 which is used for securing each flexible membrane in its exhaust port 378.

FIG. 32 shows a balanced pressure valve 436 and a further embodiment of the flexible membrane 438 including annular ribs 440 located on the internal cavity of the w membrane, which selectively stiffen the membrane against vibratory deflection away from the surface surrounding the exhaust apertures against which the membrane closes. The ribs add hoop stiffness to the membrane whilst maintaining sufficient flexibility to allow progressive or sequential deflection. In a further embodiment, annular ribs 440 could be replaced by lumps similarly located on the internal cavity, of greater thickness than the flexible membrane 438, and s thereby having greater mass and correspondingly enhancing damping by virtue of increased inertial properties.

It will be appreciated by persons skilled in the art that the balanced pressure valve 404 may take many alternate structural forms or any combination of the features previously described. Referring back to FIGS. 25 to 28, the respiratory valve apparatus 368 also includes breathable gas equilibrium passage 442 defined by a bias pressure tube 444, which is in gas flow communication between the upstream portion 388 of passage 376 and the exhaust port 378. The bias pressure tube 444 is attached to the valve body 370 by tubular barbs 446, 448 penetrating the upstream and downstream ends of the bias tube 444. Barb 446 extends upwardly from the upstream portion 388 of passage 376, and barb 448 extends centrally from the end cap 428.

During the inhalation phase (FIG. 27), when a pressurised flow of breathable gas is delivered into the valve body 370 through the inlet port 372, a volume of breathable gas is diverted into, and is maintained within, the breathable gas equilibrium passage 442, and hence within the internal cavity 412 of the flexible membrane 408, at an equilibrium pressure sufficient to maintain the flexible membrane 408 in an expanded position where it closes the exhaust apertures 28, despite a larger volume of breathable gas flowing through the breathable gas flow passage 376.

During the exhalation phase (FIG. 28), when non-return valve 386 is forced to close by the greater pressure of exhaled gas within downstream portion 392 of passage 376 than the pressure of the breathable gas entering inlet port 372, the pressure of exhaled gas within exhaled gas flow passage 382 is sufficiently greater than the equilibrium pressure of the breathable gas maintained within internal cavity 412 of flexible membrane 408 to cause the flexible membrane 408 to flexibly deform to a collapsed position and thereby open the exhaust apertures 380 so as to permit release of the exhaled gas to atmosphere.

Bias pressure tube 444 may also have a constriction 452 as shown in FIG. 25a within its internal passage or have its overall internal diameter selected so as to pneumatically dampen the response of membrane 408 during inhalation and exhalation phases. It can be appreciated that the restriction may be integral to any of the components defining the breathable Ras equilibrium passage, or alternatively an additional element added specifically for this purpose.

FIGS. 33 to 35 show alternate embodiments of a barbed end cap that may be used in the respiratory valve apparatus of the present invention. End cap 428 (used in the apparatus of FIGS. 25 to 28) has a circumferential flange 424 in the form of two external steps and end cap 426 has a circumferential flange 422 in the form of one external step. The additional external step of the flange 424 in the end cap 428 prevents inward distortion of the flange 430 of the balanced pressure valve 404, by engaging. the internal portion of the flange 430 against corresponding sides of the flange 424. The one external step of the flange 422 in the end cap 426 will, in contrast, require either adhesive bonding or frictional engagement with the flange 430 of the flexible membrane 408 to prevent such inward distortion, because end cap 426 has no features to otherwise impede inwards movement of flange 430.

It can be appreciated that while exhaust apertures 380 in the respiratory valve apparatus of FIGS. 25 to 28 are shown circumferentially around exhaust port 378 they may also be configured as depicted in earlier embodiments of first aspect of the invention, for example they may embody longitudinal slots as shown in FIGS. 9, 9a-e as previously described.

A second aspect of the respiratory valve apparatus according to the present invention is shown in FIGS. 36 to 39. The respiratory valve apparatus 454 utilises a sliding piston 456 in place of the flexible membrane 408 (of the apparatus of FIG. 25) in its balanced pressure valve.

The apparatus 454 comprises a rigid valve body 458 which includes an inlet port 460 for continuously receiving the breathable gas, and an outlet port 462 for releasing the breathable gas to the user during an inhalation phase, and for receiving exhaled gas during an exhalation phase of the user's respiratory cycle.

A breathable gas flow passage 464 (as shown by the path of the unbroken arrows in FIG. 37) communicates between the inlet port 460 and the outlet port 462.

There is an exhaust port 466 for releasing the exhaled gas to atmosphere. The exhaust port 466 includes at least one circumferential exhaust aperture 468. An exhaled gas flow passage 470 (as shown by the path of the unbroken arrows in FIGS. 38 and 39) communicates between the outlet port 462 and the exhaust port 466.

A first valve 472 is located in the passage 464 and divides that passage into an upstream portion 476 and a downstream portion 480. In this embodiment, the first valve 472 is a similar non-return valve to that used in the apparatus of FIG. 25. Like features between the valves 386 and 472 are identified by like numbers. The earlier description of the structure and function of the valve 386 also applies to the structure and function of the valve 472.

The non-return valve 472 is retained in a receptacle 474. In this embodiment, the receptacle 474 is similar to receptacle 384 used in the apparatus of FIG. 25. Like features between the receptacles 384 and 474 are identified by like numbers. The earlier description of the structure and function of the receptacle 384 also applies to the structure. and function of the receptacle 474. Additionally, receptacle 474 is presented in this embodiment as a separate attached unit, rather than the integral receptacle 384 of FIGS. 25 to 28 although it will be appreciated that similar integral configurations are possible.

As described above, the non-return valve 472 will open wider pressure of breathable gas received through the inlet port 460 during the inhalation phase (FIG. 37), and so permit flow of breathable gas to the user, and will close under pressure of exhaled gas received through the outlet port 462 during the exhalation phase (FIGS. 38 and 39), despite the maintenance of a pressurised flow of breathable gas through the inlet port 460 during the exhalation phase.

By the closing of the non-return valve 472, the exhaled gas received through the outlet port 462 is prevented from exiting through the inlet port 460, but flows through the exhaled gas flow passage 470.

A second valve 456 is located in the passage 470 and, in this embodiment, is a sliding piston and balanced pressure valve. The sliding piston 456 comprises a cylindrical body 494 having a first open end 490 and a proximal annular end lip 496 and a second closed end 492 and proximal annular lip 500.

Figure 37:
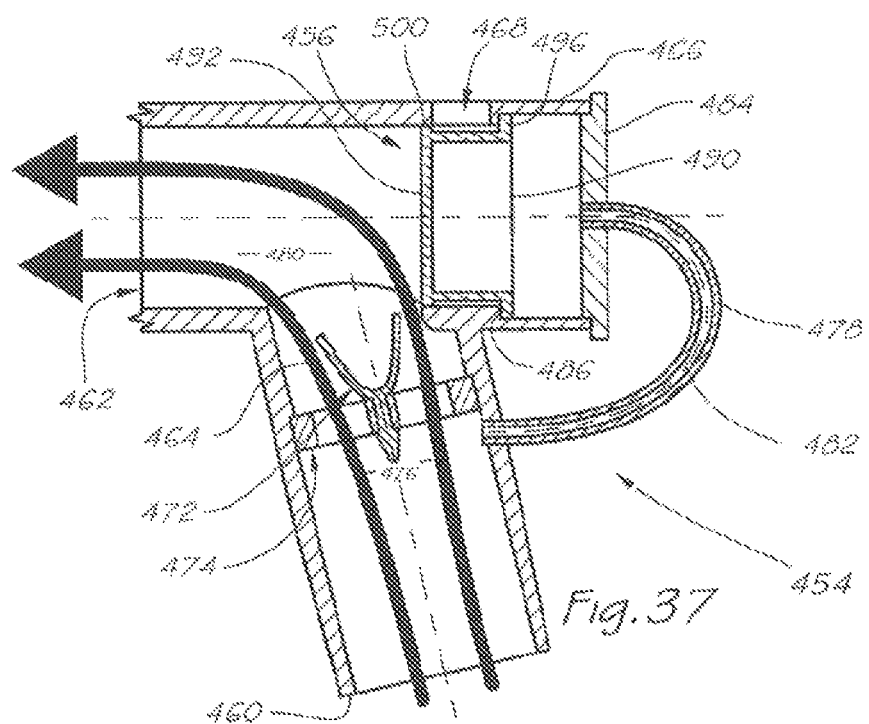
FIG. 37 is a sectional side view of a cut-away portion of the respiratory valve apparatus of FIG. 36, when assembled, and further showing the path of breathable gas during an inhalation phase.
Figure 38:
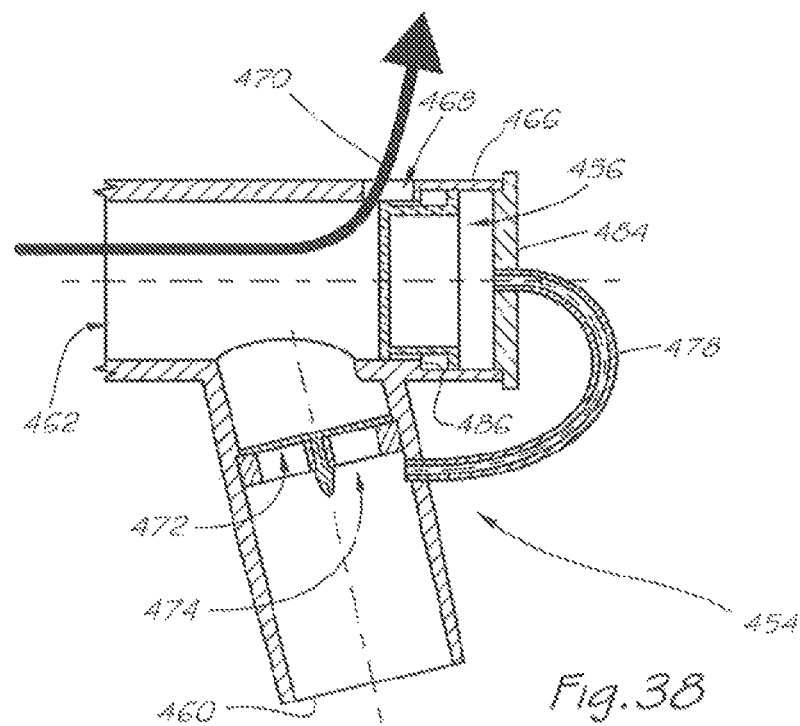
FIG. 38 is a similar view to that of FIG. 37, and further showing the path of exhaled gas during an early stage of an exhalation phase.
Figure 39:
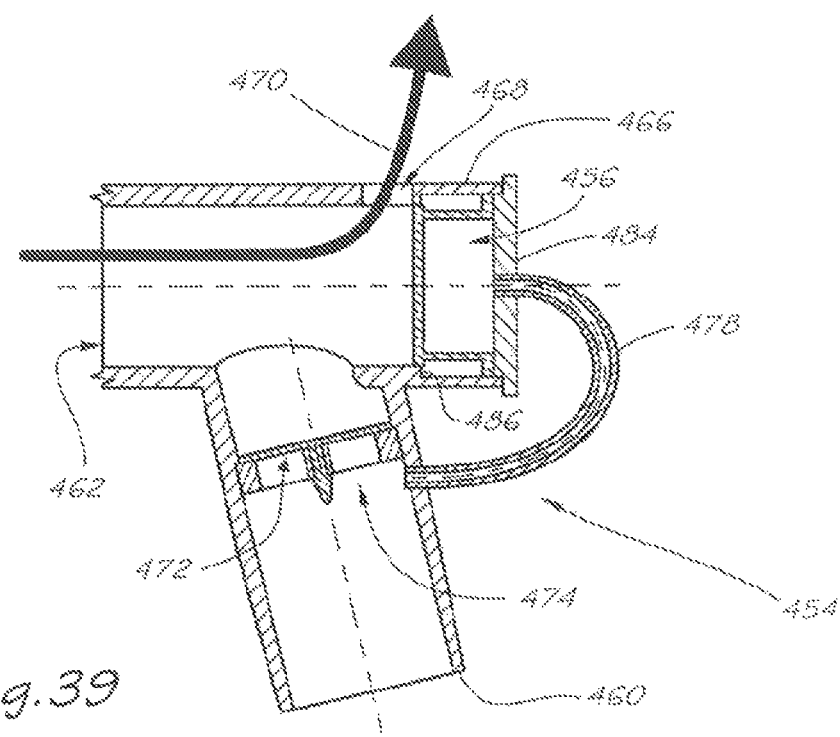
FIG. 39 is a similar view to that of FIG. 37, and further showing the path of exhaled gas during a later stage of an exhalation phase.
Figure 40:
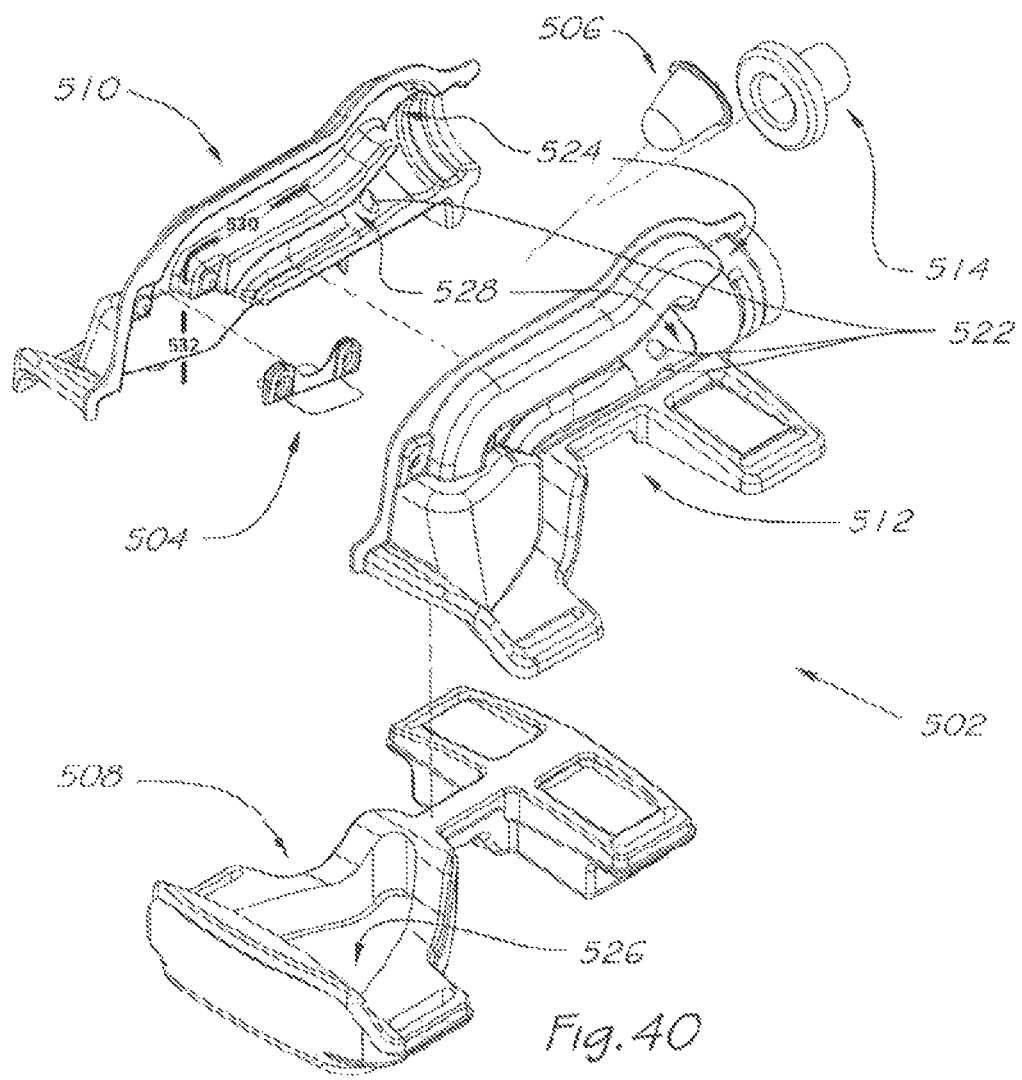
FIG. 40 is an isometric exploded view of a combined user interface and respiratory valve apparatus according to a third aspect of the present invention.
Figure 41:
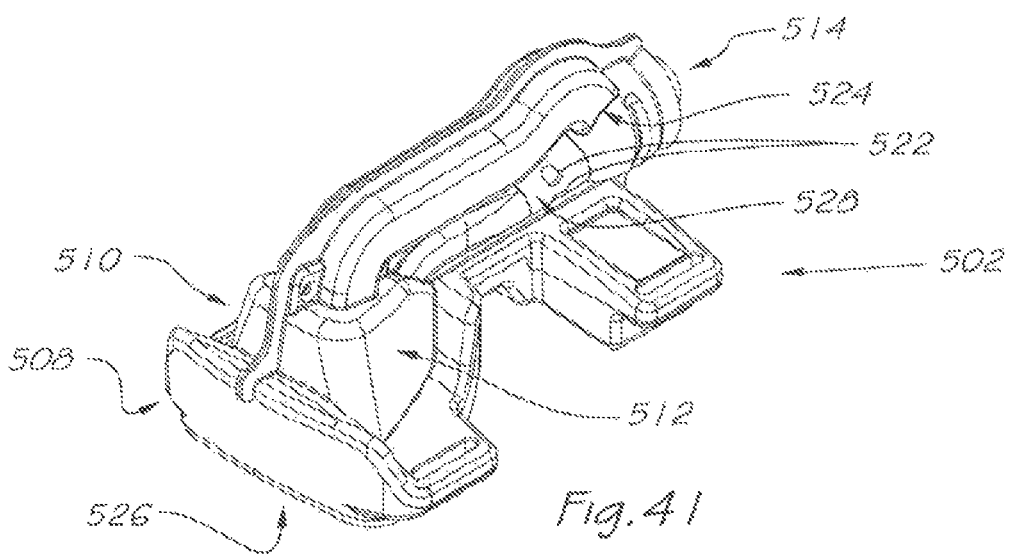
FIG. 41 is an isometric view of the combined user interface and respiratory valve apparatus of FIG. 40 in an assembled state.

The sliding piston 456 is weakly biased to a retracted position where it closes the exhaust port 466 or each exhaust. aperture 468 under ambient pressure and under pressure of breathable gas received through the inlet port 460 during the inhalation phase (FIG. 37). During the inhalation phase, the sliding piston 456 is maintained in its retracted position by the pressure applied and by annular end lip 496 which abuts against shoulder 486.

Under the pressure of exhaled gas flowing through the exhaled gas flow passage 470 during the exhalation phase (FIGS. 38 and 39), non-return valve 472 closes sealably against its receptacle 474, and the sliding piston 456 will move to an extended position so as to open the exhaust port 466 or each exhaust aperture 468, whereby the exhaled gas is released to atmosphere. In its extended position, the sliding piston 456 is located circumferentially within the inner wall of the exhaust port 466 of the valve body 458 and is retained therein by an end cap 484 having a central aperture 488. There is a breathable gas equilibrium passage 482 defined by a bias pressure tube 478, which is in gas flow communication between the upstream portion 476 of passage 464 and the exhaust port 466. The bias pressure tube 478 is attached at its respective ends to the valve body 458 by engaging through apertures 488 and 498. During the inhalation phase, when a pressurised flow of breathable gas is delivered into the valve body 458 through the inlet port 460, a volume of breathable gas is diverted into, and is maintained within, the breathable gas equilibrium passage 482 at an equilibrium pressure sufficient to maintain the sliding piston 456 in a retracted position where it closes the exhaust aperture 468, despite a larger volume of breathable gas flowing through the breathable gas flow passage 464.

During the exhalation phase, when the non-return valve 472 is forced to close by the greater pressure of the exhaled gas within the downstream portion 480 of the passage 464 than the pressure of the breathable gas entering the inlet port 460, the pressure of exhaled gas within the exhaled gas flow passage 470 is sufficiently greater than the equilibrium pressure of the breathable gas maintained within the breathable gas equilibrium passage 482 to cause the sliding piston 456 to move to an extended position where it extends away from the outlet port. 462, and thereby open the exhaust aperture 468 so as to permit release of exhaled gas to atmosphere.

It can be appreciated that while exhaust apertures 468 in the current aspect are shown circumferentially around exhaust port 466 they may also be configured as depicted in the first aspect of the invention, namely they may embody longitudinal slots as shown in FIGS. 9, 9*a-e* and as previously described.

A third aspect of the respiratory valve apparatus according to the present invention is shown in FIGS. 40 to 43. The respiratory valve apparatus 502 integrates both user interface and respiratory valve functions.

The respiratory valve apparatus 502 delivers a pressurised flow of breathable gas to the airway of the user, and comprises rigid mask and valve body left half 510 and right half 512 which are joinable and includes an inlet port 524 for continuously receiving breathable gas under pressure from the gas flow generator 14 or other ventilator device. There is an outlet port 526 which via the nasal cushion and seal interface 508, releases the breathable gas to the user's airway during an inhalation phase and receives exhaled gas during an exhalation phase of the user's respiratory cycle.

A breathable gas flow passage 516 (as shown by the path of unbroken arrows in FIG. 42) communicates between the inlet port 524 and the outlet port 526. Additional elements such as the swivel connector 514 may extend this passage.

There is an exhaust port 528 for releasing the exhaled gas to atmosphere. Exhaust port 528 includes a plurality of circumferentially spaced exhaust apertures 522.

An exhaled gas flow passage 518 (as shown by the path of unbroken arrows in FIG. 43) communicates between the outlet port 526 and exhaust port 528.

A first valve 504 is located in the breathable gas flow passage 516 and divides that passage into an upstream portion 530 and a downstream portion 532. The first valve 504 is in this embodiment a non-return valve of similar operation to valve 386 (FIG. 25). During an inhalation phase (FIG. 42) non-return valve 504 will open under pressure of breathable gas received through the inlet swivel connector 514 and then through inlet port 524 to permit a flow of breathable gas to the user, and will close under pressure of exhaled gas received through the outlet port 526 during the exhalation phase (FIG. 43), despite the maintenance of a pressurized flow of breathable gas through the inlet port 524 during the exhalation phase.

Figure 43:
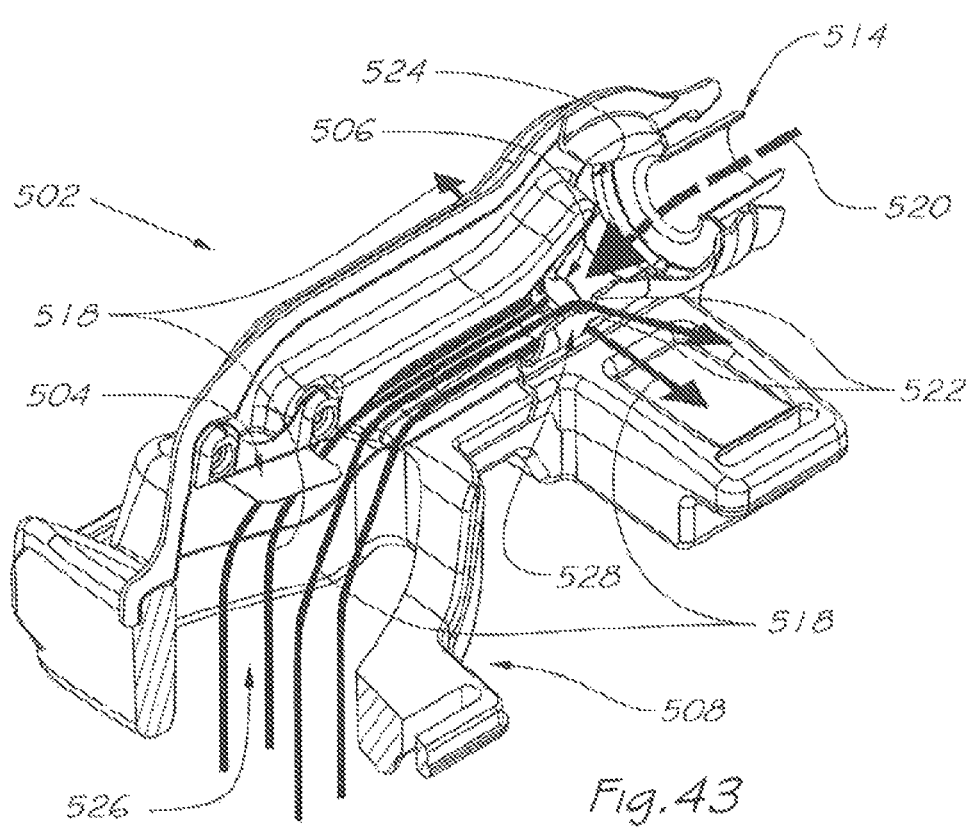
FIG. 43 is a pictorial and partly cut-away view of the respiratory valve apparatus of FIG. 40, and further showing the path of breathable gas during an exhalation phase.

By the closing of the non-return valve 504, the exhaled gas received through outlet port 526 is prevented from exiting through inlet port 524, but flows through the exhaust gas flow passage 518 (FIG. 43).

Figure 42:
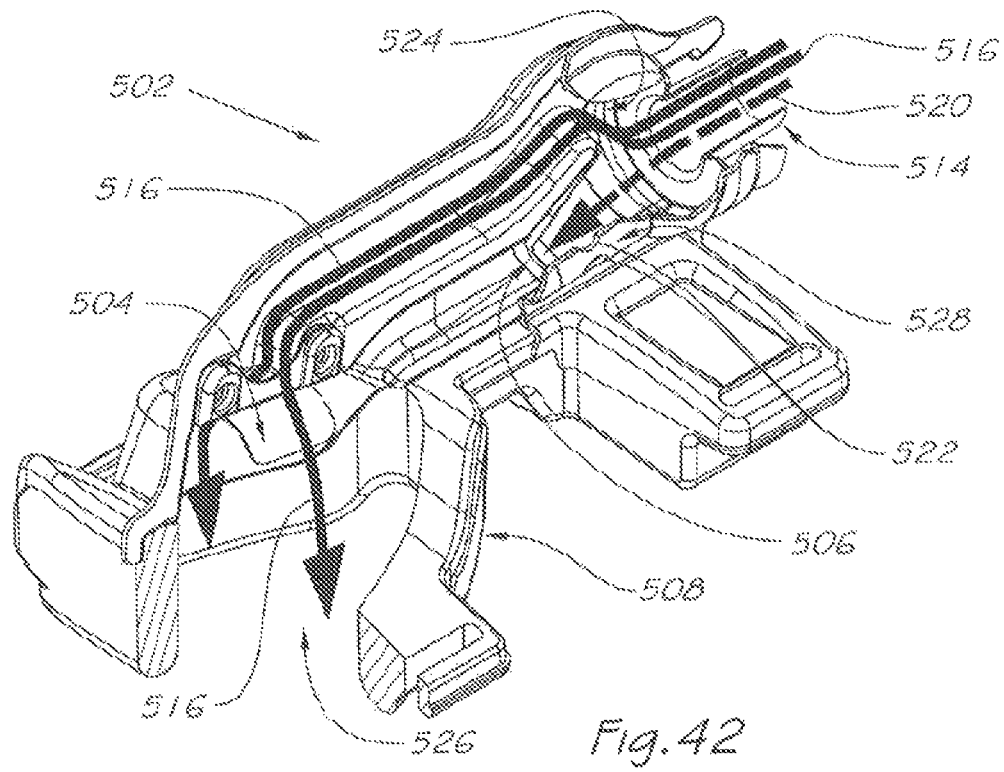
FIG. 42 is a pictorial and partly cut-away view of the respiratory valve apparatus of FIG. 40, and further showing the path of breathable gas during an inhalation phase.

A second valve 506 is located in the passage 518 and, in this embodiment, is a balanced pressure valve of similar structure and function to valve 404 (FIG. 25). The balanced pressure valve 506 closes the exhaust apertures 522 of exhaust port 528 under ambient pressure (FIG. 41) and under pressure of breathable gas received through inlet port 524 during the inhalation phase (FIG. 42). During an exhalation phase (FIG. 43), the pressure of exhaled gas flowing through the exhaled gas flow passage 518 will exceed that of the breathable gas equilibrium passage 520, causing the balanced pressure valve 506 to open the exhaust apertures 522, thereby allowing the release of exhaled gas to atmosphere.

Nasal cushion and seal interface 508 is preferably manufactured from either a solid elastomer or a foam with either closed cell structure and alternatively an outer skin, or a foam with open cell structure and an outer skin. Mask and valve body halves 510 and 512 are preferably manufactured by either vacuum forming sheet plastic or injection moulding and bonding there-between preferably achieved by either ultrasonic welding, heat staking, adhesive or the application of fasteners. Fastening of the user interface 508 and valves 504 and 506 to mask body halves 510 and 512 is preferably achieved by adhesive, however alternatives, such as overmoulding, or the use of fasteners may also be applicable.

It will be appreciated that alternative user interfaces such as full face, oronasal or nasal prong could be similarly adapted to integrate respiratory valve apparatus. Similarly, it will be appreciated that alternative non-symmetrical structural configurations could also be adopted.

It can further be appreciated that while exhaust apertures 522 in the current aspect are shown circumferentially around exhaust port 528 they may also be configured as depicted in the first aspect of the invention, namely they may embody longitudinal slots as shown in FIGS. 9, 9*a-e* and as previously described. It will be appreciated by persons skilled in the art that one advantage of the present invention in its preferred embodiments is that, in the absence of an unintentional leak from the user interface, it allows only the tidal volume of exhaled gas to be vented to atmosphere preserving administered gases, humidity and pharmacologic agents. This may also facilitate efficiencies in design and construction of accessory devices such as humidifiers and flow generators.

A still further advantage of the present invention in its preferred embodiments is that it provides substantial separation of breathable gas and exhaled gas, such that a user will not to any significant extent rebreathe exhaled gas during the full range of breathing rates and tidal volumes thereby improving the safety and efficacy of therapy. It can be appreciated that substantially eliminating accumulation of expired gas within the pressure source, by directing all tidal volume to atmosphere as described by the present invention facilitates more dynamic pressure delivery strategies to a user without increasing risk of rebreathing expired gas. For example, delivered pressure during a breathing cycle may be lower than required in the prior art, regardless of the rate and depth of breathing, to obviate rebreathing. A further example is as described in U.S. Patent Application 2009/0095297, wherein pressure is dropped during user cycled exhalation such that tidal volume is vented to atmosphere under controlled elastic recoil and immediately or soon thereafter before a user triggered inspiratory effort, pressure from the pressure source is returned to the pre-exhalation level, whereupon the cycle is repeated. Such a pressure delivery profile is facilitated by the present invention in its preferred embodiments, whereas the prior art will present significant risk of rebreathing exhaled tidal volume under these circumstances. In the case of the prior art a fraction of expired tidal volume is stored temporarily within the pressure source, in particular the pressure delivery tube. There will be insufficient time for the exhaled tidal volume so stored to be flushed to atmosphere before the pressure is automatically increased to re-inflate a user's respiratory system. On reintroduction of pressure an unacceptable proportion of expired tidal volume may be reintroduced into a user's airway and respiratory system. It can be appreciated that under these operating circumstances breathable gas from the pressure source should retain little or no expired tidal volume during lung emptying as occurs with the present invention.

It can also be appreciated that the invention in its preferred embodiments is able to maintain any delivered pressure level from the pressure source within a user's airway and that first and second valve means as described will be fully closed in absence of unintentional leaks when no user breathing effort is present, that is when there is no ingress or egress of tidal volume to or from a user's airway. For example, when the invention in its preferred embodiments is used with a constant pressure source over a. breathing cycle, that is CPAP, then a single pressure will be effectively maintained Within a user's airway, subject to any associated pressure fluctuations or swings associated with a user's inspiratory and expiratory efforts. However, there will be no flow in the inlet or outlet ports when pressures from the source and within a user's airway are equal. If however the pressure from the source is reduced during a breathing cycle from an upper pressure as may be the case during bi-level therapy, then lung volume will be elastically reduced and the volume of displaced air will be expelled and flow through the outlet port of the invention. Once pressures within a user's airways and lungs have equilibrated with the pressure source, this new pressure will again be maintained in the user's airway until another pressure is established by the pressure source. For example, if the pressure were to be then increased by the pressure source, breathable gas would correspondingly flow from the inlet port into the user's airway thereby reinflating the lungs and establishing and maintaining a new upper pressure level. A further safety advantage of the present invention in its preferred embodiments apparent from the preceding descriptions is that it may also function as a non-rebreathing valve (i.e. in an anti-asphyxia device) if the pressure source fails to generate sufficient flow to provide adequate ventilation to a user. This may occur for example during power, electrical or mechanical failure. Under such circumstances, during exhalation the non-return valve will remain closed and air will be directed to atmosphere through the exhaust apertures as the flexible membrane of the balanced pressure valve is deflected to the open position by exhaled flow. On inspiration, the balanced pressure valve will remain open, since no positive bias pressure is available from the pressure source. In normal operation, negative pressure during inhalation within the user interface will be low enough not to cause the flexible membrane of the balanced pressure valve to close the exhaust apertures and atmospheric air will be inhaled through those apertures. Alternatively, should the flexible membrane reinflate due to sufficiently negative pressure in proximity to the exhaust apertures on strong inhalation, breathable gas can also passage unidirectionally through the non-return valve allowing the user to draw unpressurised breathable gas from the pressure source providing it is of a fan, impellor or other open type.

A still further advantage of the present invention in its preferred embodiments is that exhaled gas from a user is vented to atmosphere at a lower volumetric rate of flow relative to the prior art when using continuous venting of source pressurised gas. In lowering the flow rate of exhaled gas, the present invention in its preferred embodiments minimizes the dispersion of infectious particles along with the risk of cross-infection. The invention in its preferred embodiments provides a number of benefits over continuous venting of source pressurised gas as described in the prior art. These benefits include:

Reduced carbon dioxide rebreathing as source pressure decreases or breathing rate and depth increases providing improved therapy safety and efficacy Provides more efficient use of breathable gas from a source of pressurised gas Only tidal volume of exhaled gas is vented to atmosphere preserving administered gases, humidity or pharmacologic agents May reduce transmission of exhaled infectious particles with the exhaled gas stream Minimises flow of pressurized gas onto adjacent bed partner when used in the home care setting Provides improved safety in case of power or general failure of source of pressurized breathable gas without need for additional non rebreathing valves When used with positive pressure sealing interface means such as endotracheal tube or tracheostomy the invention in its preferred embodiments is able to provide exhalation of tidal volume without need for source controlled exhalation valves reducing complexity and reliability of treatment with minimal noise from exhaled gas flow.

It will be readily apparent to persons skilled in the art that various modifications may be made in details of design, construction and operation of the respiratory valve apparatus described above without departing from the scope or ambit of the present invention.

The invention claimed is:

1. A respiratory valve apparatus for delivering a pressurised flow of breathable gas to the airway of a user, the respiratory valve apparatus comprising:
a valve body including an inlet port for receiving the breathable gas, an outlet port for releasing the breathable gas to the user's airway during an inhalation phase and for receiving exhaled gas during an exhalation phase of the user's respiratory cycle, a breathable gas flow passage communicating between the inlet and outlet ports, an exhaust port for releasing the exhaled gas, and an exhaled gas flow passage communicating between the outlet and exhaust ports, the exhaust port defining a plurality of substantially parallel slots spaced circumferentially around the valve body at the exhaled gas flow passage;

a first valve located in the breathable gas flow passage and being operable under the pressurised flow of breathable gas from the inlet port to open the breathable gas flow passage during the inhalation phase to enable flow of the breathable gas to the user, and to close the breathable gas flow passage during the exhalation phase;

a second valve located in the exhaled gas flow passage and including a flexible membrane having a sock-like structure comprising a closed end defining an internal cavity, the flexible membrane being operable to seal the exhaust port by extending, substantially parallel to the valve body, across and against the exhaust port under neutral pressure and during the inhalation phase and to at least partly expose and open the exhaust port during the exhalation phase;

an equilibrium passage disposed between an upstream side of the first valve and the internal cavity of the second valve and being operable under the pressurised flow of breathable gas from the inlet port to divert part of the breathable gas to the internal cavity of the flexible membrane via the equilibrium passage and to maintain the exhaust port closed during the inhalation phase.

2. A respiratory valve apparatus according to claim 1, wherein the plurality of slots are staggered in length.

3. A respiratory valve apparatus according to claim 1, wherein each of the plurality of slots is longitudinally tapered in thickness to become progressively narrower in an upstream direction.

4. A respiratory valve apparatus according to claim 1, wherein the flexible membrane is a flexible synthetic polymeric film of a thickness less than 0.25 millimeters.

5. A respiratory valve apparatus according to claim 4, wherein the synthetic polymeric film is polyethylene of a thickness less than 50 μm.

6. A respiratory valve apparatus according to claim 1. wherein the sock-like structure of the flexible membrane comprises an outer surface shaped substantially complementary to an inner cylindrical wall of the valve body against which it seals.

7. A respiratory valve apparatus according to claim 6, wherein the sock-like structure is tapered in shape with the flexible membrane becoming progressively smaller in circumference from its open end to its closed end.

8. A respiratory valve apparatus according to claim 6, wherein the sock-like structure is tapered in shape with the flexible membrane becoming progressively larger in circumference from its open end to its closed end.

9. A respiratory valve apparatus according to claim 8, wherein the sock-like structure comprises an expanded annular sealing portion at or adjacent to its closed end.

10. A respiratory valve apparatus according to claim 1, wherein the valve body comprises a heat and moisture exchange (HME) element coupled to the outlet port to capture moisture from the exhaled gas and transfer the moisture at least in part to the breathable gas.

11. A respiratory valve apparatus according to claim 1, wherein the equilibrium passage is defined by a bias pressure passage.

12. A respiratory valve apparatus according to claim 11, wherein the bias pressure passage comprises a bias pressure tube.

13. A respiratory valve apparatus according to claim 11, wherein the bias pressure passage is restricted to dampen operation of the second valve.

14. A respiratory valve apparatus according to claim 1, wherein the valve body comprises a swivel connector at the inlet port, the first valve being connected to the swivel connector.

15. A respiratory valve apparatus according to claim 14, wherein the first valve is a non-return valve comprising a flexible flap connected to the swivel connector.

16. A respiratory valve apparatus according to claim 15, wherein the swivel connector comprises a central post to which the flexible flap is mounted.

17. A respiratory valve apparatus according to claim 1, further comprising a user interface connected to the valve body.

18. A respiratory valve apparatus according to claim 17, wherein the user interface is integral with the valve body.

19. A respiratory valve apparatus for delivering a pressurised flow of breathable gas to the airway of a user, comprising:

a valve body comprising an inlet port configured to receive the breathable gas, an outlet port configured to release the breathable gas to the user's airway during an inhalation phase and to receive exhaled gas during an exhalation phase of a respiratory cycle of the user, a breathable gas flow passage communicating between the inlet and outlet ports, an exhaust port for releasing the exhaled gas, and an exhaled gas flow passage communicating between the outlet and exhaust ports;

the exhaust port defining a plurality of substantially parallel slots spaced circumferentially around the valve body at the exhaled gas flow passage, the slots being staggered in length;

a first valve located in the breathable gas flow passage and being configured under the pressurised flow of breathable gas from the inlet port to open the breathable gas flow passage during the inhalation phase to enable flow of the breathable gas to the user, and to close the breathable gas flow passage during the exhalation phase;

a second valve located in the exhaled gas flow passage and including a flexible membrane that defines an internal cavity, the flexible membrane being configured to close the exhaust port under neutral pressure and during the inhalation phase and to at least partially open the exhaust port during the exhalation phase;

an equilibrium passage disposed between an upstream side of the first valve and the internal cavity of the second valve and being configured, under the pressurised flow of breathable as from the inlet port, to divert part of the breathable gas to the internal cavity of the flexible membrane via the equilibrium passage to neutral pressure and to maintain the exhaust port closed during the inhalation phase.

20. A respiratory valve apparatus for delivering, a pressurised flow of breathable gas to the airway of a user, comprising:

a valve body comprising an inlet port configured to receive the breathable gas, an outlet port configured to release the breathable gas to the user's airway during an inhalation phase and to receive exhaled gas during an exhalation phase of the user's respiratory cycle, a breathable gas flow passage communicating between the inlet and outlet ports, an exhaust port configured to release the exhaled gas, and an exhaled gas flow passage communicating between the outlet and exhaust ports;

the exhaust port defining a plurality of substantially parallel slots spaced circumferentially around the valve body at the exhaled gas flow passage, each of the slots being longitudinally tapered in thickness and progressively narrower in an upstream direction;

a first valve located in the breathable gas flow passage and being, configured, under the pressurised flow of breathable gas from the inlet port, to open the breathable gas flow passage during the inhalation phase to enable flow of the breathable gas to the user, and to close the breathable gas flow passage during the exhalation phase;

a second valve located in the exhaled gas flow passage and comprising a flexible membrane defining an internal cavity, the flexible membrane being: configured, under neutral pressure and during the inhalation phase, to close the exhaust port and, during the exhalation phase, to at least partly open the exhaust port;

an equilibrium passage disposed between an upstream side of the first valve and the internal cavity of the second valve and being configured, under the pressurised flow of breathable gas from the inlet port, to divert part of the breathable gas to the internal cavity of the flexible membrane via the equilibrium passage to neutral pressure and, during the inhalation phase, maintain the exhaust port closed.

21. The respiratory valve apparatus of claim 20, wherein the plurality of substantially parallel slots are staggered in length at the exhaled gas flow passage.

* * * * *